United States Patent [19]
Li et al.

[11] Patent Number: 5,710,019
[45] Date of Patent: Jan. 20, 1998

[54] HUMAN POTASSIUM CHANNEL 1 AND 2 PROTEINS

[75] Inventors: Yi Li, Gaithersburg; Mark D. Adams, North Potomac; Owen R. White, Gaithersburg, all of Md.

[73] Assignee: Human Genome Sciences, Inc., Gaithersburg, Md.

[21] Appl. No.: 464,340

[22] Filed: Jun. 5, 1995

[51] Int. Cl.⁶ .......................... C12P 21/02; C12N 15/12; C07K 14/705
[52] U.S. Cl. .................. 435/69.1; 435/240.2; 435/252.3; 435/325; 435/530; 435/350; 435/536; 435/23.5
[58] Field of Search .......................... 435/69.1, 240.2, 435/252.3, 325; 530/350; 536/23.5

[56] References Cited

U.S. PATENT DOCUMENTS 5,492,825  2/1996  Jan et al. ........................ 435/240.2

FOREIGN PATENT DOCUMENTS

WO 92/02634  2/1992  WIPO .
WO 93/22422  11/1993  WIPO .

OTHER PUBLICATIONS

Beckh, et al., The EMBO Journal, vol. 9, No. 3 pp. 777–782. (1990).

Hwang, et al., Neuron, vol. 8, 473–481, (Mar. 1992).

Schwarz, et al., Nature, vol. 331 (Jan. 14, 1988) pp. 137–142.

Pak, et al., Proc. Natl., Acad. Sci. USA, vol. 88, pp. 4386–4390 (May 1991).

Milkman, Proc. Natl. Acad. Sci. USA, vol. 91, pp. 3510–3514 (Apr. 1994).

Drewe, et al., The Journal of Neuroscience, 12(2):538–548 (Feb. 1992).

Isacoff et al., Annals New York Academy of Sciences vol. 707(1993) pp. 51–59.

*Primary Examiner*—Stephen Walsh
*Assistant Examiner*—Daryl A. Busham
*Attorney, Agent, or Firm*—Elliot M. Olstein; J. G. Mullins

[57] ABSTRACT

Disclosed are human $K_+$ channel polypeptides and DNA (RNA) encoding such $K_+$ channel polypeptides. Also provided is a procedure for producing such polypeptides by recombinant techniques. Agonists for such $K_+$ channel polypeptides are also disclosed. Such agonists may be used to treat epilepsy, stroke, hypertension, asthma, Parkinson's disease, schizophrenia, anxiety, depression and neurodegeneration. Also disclosed are antagonists against such polypeptides which may be used to treat AIDS, SLE, diabetes, multiple sclerosis and cancer. Also disclosed are diagnostic assays for detecting mutations in the polynucleotide sequences of the present invention.

14 Claims, 11 Drawing Sheets

FIG. 1A

ACAAAAGCTGGAGCTCCACCGCGTGCGGCCGCTCTAGAACTAGTGGATCCCCCGGCTG
CAGGGCTCCGAGGGGGAGCTGAGCCGGGGAGCCCCGGGGAAGTTTGGCGGCGGCTCC
GGGAGGCAGAGCGGGCTCCCCGGGGACTTCCAGGCCCCCTCTCGCTCCTCGCCCCGAC
CCGTGGGCAGTCGGGGGGACGGAAGCCGCGGCCAACTCCGAGGCGGGACGCCG
CGACGGGAACTTGAGGCCCGAGAGGGATGTGAAGGCCCAAAATGACCCTCTTACCGGGAG
                                   M  T  L  L  P  G  D
ACAATTCTGACTACGACTACAGCGCGCTGAGCTGCACCTCGGACGCCTCCTTCCACCCGG
 N  S  D  Y  D  Y  S  A  L  S  C  T  S  D  A  S  F  H  P  A
CCTTCCTCCCGCAGCGCCAGCAGGCCATCAAGGGCGCGTTCTACCGCGCCCAGCGGCTGC
 F  L  P  Q  R  Q  A  I  K  G  A  F  Y  R  A  Q  R  L  R
GGCCGCAGGATGAGCCCCGCCAGGGCTGTCAGCCCGAGGACCGCCGTCGGATCATCA
 P  Q  D  E  P  R  Q  G  C  Q  P  E  D  R  R  R  R  I  I  H
TCAACGTAGGCGGCATCAAGTACTCGCTGCCCTGGACCACGCTGGACGAGTTCCCGCTGA
 I  N  V  G  G  I  K  Y  S  L  P  W  T  T  L  D  E  F  P  L  T
CGGCGCCTGGCCCAGCTGAAGGCCTGCAACGAGTTCTTCTTCGACAGATCCTCAACGTGTGCGATG
 R  L  G  Q  L  K  A  C  T  N  E  F  F  F  D  D  I  L  N  V  C  D  D
ACTACGACGTCACCTGCAACGAGTTCTTCTTCGACAGGAACCCGGGCGCCTTCGGCACTA
 Y  D  V  T  C  N  E  F  F  F  D  R  N  P  G  A  F  G  T  I
TCCTGACCTTCCTGCGCGCGAAGCTGCGGCTGCGCGAGATGTGCGCGCTGTCCT
 L  T  F  L  R  A  G  K  L  R  L  R  E  M  C  A  L  S  F
TCCAGGAGGAGCTGCTGTACTGGGGCATCGCGGAGGACCACCTGGACGGCTGCAAGC
 Q  E  E  L  L  Y  W  G  I  A  E  D  H  L  D  G  C  K  R
GCCGCTACCTGCAGAAGATTGAGGAGTTCGCGGAGATGGTGGAGCGGGAAGAGGACG
 R  Y  L  Q  K  I  E  E  F  A  E  M  V  E  R  E  E  E  D

FIG. 1B

```
ACGCGCTGGACAGCGAGGGCCGGCCGAGGCCGAGGGCCGCTGG
 A  L  D  S  E  G  R  D  S  E  G  P  A  E  G  E  G  R  L  G
GGCGGTGCATGCGGCGACTGCGCGACATGGTGGAGAGGCCACTCGGGGCCTGGCA
 R  C  M  R  R  L  R  D  M  V  E  R  P  H  S  G  L  P  G  K
AGGTGTTCGCGCTGTCCGTGCTCTTCGTGACCGTCAACCTCTCCGTCA
 V  F  A  C  L  S  V  L  F  V  T  V  T  A  V  N  L  S  V  S
GCACCTTGCCCAGCCTGAGGAGGAGGAGGAGCAGGGCCACTGTTCCCAGATGTGCCACA
 T  L  P  S  L  R  E  E  E  E  Q  G  H  C  S  Q  M  C  H  N
ACGTCTTCATCGTGGAGTCGGTGTGCGTGGTTCTCCCTGGAGTTCCTCCTGCGGC
 V  F  I  V  E  S  V  C  V  G  W  F  S  L  E  F  L  L  R  L
TCATTCAGGCGCCCAGCAAGTTCGCCTTCCTGCGGAGCCCGCTGACGCTGATCGACCTGG
 I  Q  A  P  S  K  F  A  F  L  R  S  P  L  T  L  I  D  L  V
TGGCCATCCTGCCCTACTACATCACGCTGGTGGATGGGGCCGCAGCCGGTCGCA
 A  I  L  P  Y  Y  I  T  L  V  D  G  A  A  A  G  R  R  K
AGCCCGGCGCGGGCAACAGCTACCTGGACAAGTGGGGCCTGGTGCGCGTGCTGCGGG
 P  G  A  G  N  S  Y  L  D  K  V  G  L  V  R  V  L  R  A
CGCTGCGCCATCCCTGTACGTGATGCGCCTGGCCACTCCCTGGGCTGCAGACGCTGG
 L  R  I  L  Y  V  M  R  L  A  R  H  S  L  G  L  Q  T  L  G
GGCTCAAGGCCCGCTGCTGCTGCTGCTGCTGTTCCTGTGCGTCGCTGTGG
 L  T  A  R  R  C  T  R  E  F  G  L  L  L  F  L  C  V  A
CCATCGCCCTCTTCGCGCCCCTGCTCTACGTCATCGAGAACGAGATGGCCGACAGCCCCG
 I  A  L  F  A  P  L  L  Y  V  I  E  N  E  M  A  D  S  P  E
AGTTCACCAGCATCCCTGCCTGCTACTGGGCTGTCATCACCACGACGGTGGACT
 F  T  S  I  P  A  C  Y  W  A  V  I  T  M  T  T  V  D  Y
ATGGCGACATGGTCCCCAGGAGCACCCCGGGCCAGGTAGTGGCCCTGAGCATCCTGA
 G  D  M  V  P  R  S  T  P  G  Q  V  V  A  L  S  S  I  L  S
```

FIG. 1C

```
GCGGCATCCTGCTCATGGCCTTCCCAGTCACCTCCATCTTCCACACCTTCTCCCCTCCT
 G  I  L  L  M  A  F  P  V  T  S  I  F  H  T  F  S  P  S  Y
ACCTGGAGCTCAAACAGGAGCAAGAGGAGCAAGAGGGTGATGTTCCGAGGGCAGTTCCTCATCA
 L  E  L  K  Q  E  Q  E  R  V  M  F  R  R  A  Q  F  L  I  K
AAACCAAGTCGCAGTCGAGCTGTCCCAGGACAGTGACATCTTGTTCGGAAGTGCCTCCT
 T  K  S  Q  L  S  V  S  Q  D  S  D  I  L  F  G  S  A  S
CGGACACCAGAGACAATAACTGAGCGCGGAGGACACGCCCTGCCTGCCATCTGTGG
 D  T  R  D  N  N  *
CCCGAAGCCATTGCCATCCACTGCAGACGCCTGGAGAGGGACAGGCCGCTTCCGAGTGCA
GTCCTGGCGCAGCAGCACCGACTCCCACGCACTCCACGCAAGGACACCCTCACTCCCACACCCC
GGGAAGAACACTAGAACATCAGCAGCAGACCCGCCAGCCCTCCGCAGCCGTGAAAGG
AAGCTGGGTCATCAGCCCAGCCCTCATCAGCCCCCAGCCCCCTATGTGTTTCCCTGCAATAA
GGAGATGCCTTGTTCTTTCTTTTCACCATGC
```

FIG. 2A

```
         10                        30                        50
GGTCGCAACCCCCTCGGTGACCCGCTGCGCCCGAGGAGGGGCCGGCGGTGCGGGTGGTGG
         70                        90                       110
CGGCGGGCGCGGCAGCTGTGCCCCGTCTGCCCCCAAGGGGTTAATCCGTCCCCTGCAGCTGCCG
        130                       150                       170
CGCGTGCCTTGCAGAATTTCACCAGAAGAGGGTACAGTTTGAAAAGCTCCTGACGTCAGG
        190                       210                       230
CTGGAATTCCTATTGTGTTTAGAAAAGGCTCGGGCAAAGCCAGCCCAAGTTCGCTCTCTG
        250                       270                       290
CACACCTCGAGCACCTCGGGACGGCGGTGGGTCCGCCCAGCTCCGGGACCTGCGCCGCTG
        310                       330                       350
CCTGCGCGCCCCGGGGCGGAGGACGGCGGGAGCGCGCCAGCCGCCACGAGGAGACCCCGCA
        370                       390                       410
GGAGGCCGAGCTGAAGCGGCCCGCCAAAGCCCCGGGGTTCGTCCCGGGGTGAGTGCCCCGGGCG
        430                       450                       470
AGGCCGGGCGGCCCGCCAAAGCCCCGGGGTTCGTCCCGGGGATGCCAGCCCCCGAG
        490                       510                       530
CCCCGCCCGGGGTGCATGCCTCCCCCGCGCGGGGCCAGGCTGCCCCGCAGCCCCCGAG
        550                       570                       590
ACCGCCCTTCCCCGGGGCAGGCTCTCCCACGAGATACGACGCACGGGT
        610                       630                       650
GGCACCCCGCCGACCCCCAACGACAACGGCGACGTCTGCAGGGGCGGGGGCCGGAG
        670                       690
                                  710
```

FIG. 2B

```
CCTGCGAGGGCGCACGGGGAGGAGGATGGACGGGTCCGGGGAGCGAGCCTCCCCGGAGCCG
                        M  D  G  S  G  E  R  S  L  P  E  P
              730                   750                   770
GGCAGCCAGAGCTCCCGCTGCCAGCGACGACATAGAGATAGTCGTCAACGTGGGGGCGTG
 G  S  Q  S  S  A  A  S  D  D  I  E  I  V  V  N  V  G  G  V
              790                   810                   830
CGGCAGGTGCTGTACGGGGACCTCCTCAGTCAGTACCCTGAGACCCGGCTGGCCGAGCTC
 R  Q  V  L  Y  G  D  L  L  S  Q  Y  P  E  T  R  L  A  E  L
              850                   870                   890
ATCAACTGCTTGGCTGGGGGCTACGACACCATCTTCTCCCTGTGCGACGACTACGACCCC
 I  N  C  L  A  G  G  Y  D  T  I  F  S  L  C  D  D  Y  D  P
              910                   930                   950
GGCAAGCGCGAGTTCTACTTTGACAGGGACCCGGACGCCTTCAAGTGTGTCATCGAGGTG
 G  K  R  E  F  Y  F  D  R  D  P  D  A  F  K  C  V  I  E  V
              970                   990                  1010
TACTATTTCGGGGAGGTCCACATGAAGAAGGGCATCTGCCCCATCTGCTTCAAGAACGAG
 Y  Y  F  G  E  V  H  M  K  K  G  I  C  P  I  C  F  K  N  E
             1030                  1050                  1070
ATGGACTTCTGGAAGGTGGACCTCAAGTTCCTGGACGACTGTTGCAAGAGCCACCTGAGC
 M  D  F  W  K  V  D  L  K  F  L  D  D  C  C  K  S  H  L  S
             1090                  1110                  1130
GAGAAGCGCGAGGAGCTGGAGGAGATCGCCCGTCGCGTGCAGCTCATCCTGGACGACCTG
 E  K  R  E  E  L  E  E  I  A  R  R  V  Q  L  I  L  D  D  L
```

FIG. 2C

```
         1150                1170                1190
GGCGTGGACGGCGCCGAGGGCCGCTGGCGCCGCTGCCAGAAGTGCGTCTGGAAGTTCCTG
 G  V  D  A  A  E  G  R  W  R  R  C  Q  K  C  V  W  K  F  L
         1210                1230                1250
GAGAAGCCCGAGTCGTGCCCGGCGCGGGTGGCCGAGCTCTCCTTCCTGCTCATC
 E  K  P  E  S  C  P  A  R  V  A  E  L  S  F  L  L  I
         1270                1290                1310
CTCGTCTCGTCCGTGGTCTGCATGGACACCATCCCCGAACTGCAGGTGCTGGACGCC
 L  V  S  S  V  V  C  M  D  T  I  P  E  L  Q  V  L  D  A
         1330                1350                1370
GAGGGCAACCGCGTGGAGCACCCGACGCTGGAGAACGTGGAGACGGCGTGCATTGGCTGG
 E  G  N  R  V  E  H  P  T  L  E  N  V  E  T  A  C  I  G  W
         1390                1410                1430
TTCACCCTGGAGTACCTGCTCCTCCGTCTGTTCTCGTCACCCAACAAGCTGCACTTCGCGCTG
 F  T  L  E  Y  L  L  R  L  F  S  S  P  N  K  L  H  F  A  L
         1450                1470                1490
TCCTTCATGAACATTGTGGTGGTGCTGGCCATCCTCCCCTTCTACGTGAGcTTGACGCTC
 S  F  M  N  I  V  V  V  L  A  I  L  P  F  Y  V  S  L  T  L
         1510                1530                1550
ACGCACCTGGGTGCCCGCATGATGGAGCTGACCAACGTGCAGCAGGCCGTGCAGGCCCTG
 T  H  L  G  A  R  M  M  E  L  T  N  V  Q  Q  A  V  Q  A  L
```

FIG. 2D

```
         1570                          1590                          1610
CGGATCATGCGGCATCGGCGCGCATCTTCAAGCTTCAAGCGCCACTCCCTGGGCCTGCAGACC
 R   I   M   R   I   A   R   I   F   K   L   A   R   H   S   S   G   L   Q   L
                     1630                          1650                          1670

CTCACCTATGCCCTCAAGCGCAGCTTCAAGGAACTGGGGCTGCTGCTCATGTACCTGGCA
 L   T   Y   A   L   K   R   S   F   K   E   L   G   L   L   L   M   Y   L   A
                     1690                          1710                          1730

GTGGGTATCTTCGTCTTCTCTGCCCTGGGCTACACCATGGAGCAGAGCCATCCAGAGACC
 V   G   I   F   V   F   S   A   L   G   Y   T   M   E   Q   S   H   P   E   T
                     1750                          1770                          1790

CTGTTTAAGAACATCCCCCAGTCCTTCTGGTGGGCCATCATCACCATGACCACCGTCGGC
 L   F   K   N   I   P   Q   S   F   W   W   A   I   I   T   M   T   T   V   G
                     1810                          1830                          1850

TACGGCGACATCTACCCCAAGACCACGCTGAGCAAGCTCAACGCGGCCATCAGCTTCTTG
 Y   G   D   I   Y   P   K   T   T   L   S   K   L   N   A   A   I   S   F   L
                     1870                          1890                          1910

TGTGGTGTGCATTGCCATCGCCCTGCCCATCCACCCCATCATCAACAACTTTGTCAGGTAC
 C   G   V   I   A   I   A   L   P   I   H   P   I   I   N   N   F   V   R   Y
                     1930                          1950                          1970

TACAACAAGCAGCGCGTCCTGGAGACCGCCAAGCACGAGCTGGAGCTGATGGAACTC
 Y   N   K   Q   R   V   L   E   T   A   K   H   E   L   E   L   M   E   L
                     1990                          2010                          2030

AACTCCAGCAGCGGCGAGGGCAAGACCGGGGCTCCCCGAGTGACCTGACAACCTC
 N   S   S   S   G   G   E   G   K   T   G   G   S   R   S   D   L   D   N   L
```

FIG. 2E

```
      2050                  2070                 2090
CCTCCAGAGCCTGCGGGGAAGGAGGCGCCGAGCTGCAGCAGCCGGCTGAAGCTCTCCCAC
  P  P  E  P  A  G  K  E  A  P  S  C  S  S  R  L  K  L  S  H
                       2110                 2130                 2150
AGCGACACCTTCATCCCCCTCCTGACCGAGGAGAAGCACCACAGGACCCGGCTCCAGAGT
  S  D  T  F  I  P  L  L  T  E  E  K  H  H  R  T  R  L  Q  S
                       2170                 2190                 2210
TGCAAGTGACAGGAGGGCCCCTCAGGCAGAGATGGACCAGGCGGTGGACAGATGGGTAGAT
  C  K  *
           2230                 2250                 2270
GTGGCAGGCATGTCATCGACACAGCACACAGAGGGCTGTCCCCCTGTGTCCCCCAACCCCTCCCCT
                 2290                 2310                 2330
GGACAGACTCTGAAGGCCCTCTCCGGACCCTTCGCCAAGGCTGGGTAAGACTCCTCTATGT
                 2350                 2370                 2390
TGCCTGCTGTGTCCAGGAGCCGGGAGGGGTGTGCAGGAGCCCAGGAGCCCAGGCCGTGTGGGA
                 2410                 2430                 2450
CGAGTGGAGGCCGGCCTGGCCTGGCTGGCACGAGAGCCCACGCCCCGCTTCTGTATCTCCCTCA
                 2470
ATAAAGCCTCCTGCTCTGTGCAA
```

FIG. 3A

```
  4  SGERSLPEPGSOSSAASDDIEIV............VNVGGVRQVLYGDLLSQ   43
  2  ......PAGMTKHGSRSTSSLPPEPMEIVRSKACSPRVRLNVGGLAHEVLWRTLDR  51
 44  YPETRLAELINCLAGGYDTIFSBCDDYDPGKREFYFDRDPDAFKCVIEVY        93
 52  LPRTRLGKLRDC..NTHDSLLEVCDDYSLDDNEYFFDRHPGAFTSILNFY        99
 94  YFGEVHMKKGICPICFRNEMDFWKVDLKFLDDCCKSHLSEKREELEEIAR       143
100  RTGRLHMMEEMCALSFSQELDYWGIDEIYLESCCQARYHQKKEQMNEELK       149
141  RVQLIL.....DDLGVDAAEGRWRRCQKCVWKFLEKPESSCPARVVAELS       188
150  REAETLREREGEEFDNTCCAEKRKK....LWDLLEKPNSSVAAKILAIIS       195
```

FIG. 3B

```
189  FLLILVSSVVMCMDTIPELQVLDAEGNRVEHPTLENVETACIGWFTLEYL  238
     :.:  :.  :::.  : .:   ..       .    :  :::::
196  IMFIVLSTIALSLNTLPELQSLDEFGQSTDNPQLAHVEAVCIAWFTMEYL  245

239  LRLFSSPNKLHFALSFMNIVDVLAILPFYVSLTLTHLGARMMELTNVQQA  288
     ::::::: :  : : :::::::::::  : :::: :    :::: ..
246  LRFLSSPKKWKFFKGPLNAIDLLAILPYYVTIFLTESNKSVLQFQNVRRV  295

289  VQALRIMRIARIFKLARHSSGLQTLTYALKRSFKELGLLMYLAVGIFIF   338
     ::: ::::::::::::::: ::  :   :: ::.:: ::: : ::.::
296  VQIFRIMRILRILKLARHSTGLQSLGFTLRRSYNELGLLILFLAMGIMIF  345

339  SALGYTMEQSHPETLFKNIPQSFWWAIITMTTVGYGDIYPKTTLSKLNAA  388
      :::  :       :::  ::.:::: ::::::::::::: :: :
346  SSLVFFAEKDEDDTKFKSIPASFWWATITMTTVGYGDIYPKTLLGKIVGG  395
```

FIG. 3C

```
389  ISFLCGVIAIALPIHPIINNFVRYYNKQRVLETAAK..........  424
        .  :  ||:|||||  |:|||  :.:  |||
396  LCCIAGVLVIALPIPIIVNNFSEFYKEQKRQEKAIKRREALERAKRNGSI  445

425  ..........HELELMELNSSSGGEGKTGGSRSDLDNLPP..........  454
                  |  ||  |  .|
446  VSMNMKDAFARSIEMMDIVVEKNGENMGKKDKVQDNHLSPNKWKWTKRTL  495

455  ..........EPAGKEAPSCSSRLKLSHSDTFIPLLTEEKHHRTRLQ  491

496  SETSSSSKSFETKEQGSPEKARSSSSSPQHLN..........VQQLEDMYNKMAKTQ  540
492  S————————S  492
541  S————————S  541
```

HUMAN POTASSIUM CHANNEL 1 AND 2 PROTEINS

This application is entitled to the benefits of 35 U.S.C. §120 for priority based on PCT/US94/08449, filed 28 Jul. 1994.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human potassium channel proteins sometimes hereinafter referred to as a "$K^+$ channel 1 and 2 polypeptides." The invention also relates to inhibiting the action of such polypeptides.

Potassium channels probably form the most diverse group of ion channels, and are essential to the control of the excitability of nerve and muscle. Some potassium channels open in response to a depolarization of the membrane, others to a hyperpolarization or an increase in intracellular calcium. Some can also be regulated by the binding of a transmitter and by intracellular kinases, GTP-binding proteins or other second messengers.

Potassium channels are a heterogeneous group of ion channels that are similar in their ability to select for potassium over other ions, but differ in details of activation, inactivation and kinetics (Latorre, R. and Miller, C., J. Memb. Biol., 7:11–30. (1983)). They contribute significantly to several physiological functions, for example, action potential repolarization, cardiac pacemaking, neuron bursting, and possibly learning and memory (Hodgkin, A. L. and Huxley, A. F., J. Physiol. 117:500–544 (1952)).

The molecular basis for potassium channel function has been greatly clarified by molecular cloning in the Drosophila family members of potassium channels, designated Shaker, Shaw, Shal, and Shad (Tempel, B. L. et al., Science, 237:770–775 (1987)). Mammalian homologs for all four of these potassium channels have been cloned, (Tempel, B. L. et al., Nature, 332:837–839 (1988)). Subtypes of Drosophila potassium channels have been identified. The subtypes in Drosophila are largely derived by alternative splicing, (Schwartz, T. L. et al., Nature, 331:137–142 (1988)), whereas subtypes of mammalian potassium channels generally represent distinct genes, although splicing occurs as well. The biophysical properties of these channels can vary with only small alterations in the amino acid sequence, the principal differentiation being between slowly inactivating, "delayed rectifier" channels and rapidly inactivating, A-type channels, (Wei, A. et al., Science, 248:599–603 (1990)). Mammalian homologs of Drosophila potassium channels may display either the same or different biophysical properties.

Potassium channels are involved in normal cellular homeostasis and are associated with a variety of disease states and immune responses. Diseases believed to have a particular association with sodium, calcium and potassium channels include autoimmune diseases and other proliferative disorders such as cancers. Autoimmune diseases include rheumatoid arthritis, type-1 diabetes mellitus, multiple sclerosis, myasthenia gravis, systematic lupus erythematosus, Sjogren's syndrome, mixed connective tissue disease among others.

Several classes of potassium channels are involved in maintaining membrane potential and regulating cell volume in diverse cell types, as well as modulating electrical excitability in the nervous system (Lewis, R. S. and Cahalan, M. D., Science, 239:771–775 (1988)). Potassium channels have been shown to control the repolarization phase of action potentials and the pattern of firing neurons and other cells. Potassium currents have been shown to be more diverse than sodium or calcium currents, and also play a central role in determining the way a cell responds to an external stimulus. For instance, the rate of adaptation or delay with which a neuron responds to synaptic input is strongly determined by the presence of different classes of potassium channels. The molecular mechanisms generating potassium channel diversity are best understood in the Shaker locus from Drosophila which contains 21 exons spanning 130 kb and generates four different potassium channel proteins through alternative splicing of a single primary transcript, (DeCoursey, T. E. et al., J. Gen. Physiol. 89:379–404 (1987)). Expression of these cDNAs in Xenopus oocytes gives rise to voltage-dependent potassium currents with distinct physiological properties. The related Drosophila potassium channel gene Shab also exhibits alternative splicing of a primary transcript giving rise to two distinct proteins (McKinnon, D., and Ceredig, R., J. Exp. Med., 164:1846–1861 (1986)).

PCT Application No. WO 92/02634 discloses the n potassium channel expression product of the MK3 gene or a functionally bioactive equivalent thereof and its uses, particularly in combination with identifying immune responses and materials modulating or blocking the same.

A novel potassium channel with unique localizations in the mammalian brain has been identified, cloned and sequenced and has been designated cdrk, utilizing a cDNA library prepared from circumvallate papillae of the rat tongue. The cdrk channel appears to be a member of the Shab's subfamily, most closely resembling cdrk1. The cdrk channel may be important in a variety of excitable tissues, (Hwang, P. M., et al., Neuron, 8:473–481 (1992)).

Multiple potassium channel components have been produced by alternative splicing at the Shaker locus in Drosophila, (Schwarz, T. L., et al., Nature, 331–137–142 (1988)). Members of the RCK potassium channel family have been differentially expressed in the rat nervous system. mRNA'S encoding four members of the RCK potassium channel family, named RCK1, RCK3, RCK4 and RCK5 have been analyzed by RNA blot hybridization experiments using specific RNA probes, (Beckh, S. and Pongs, O., The EMBO Journal, 9:777–782 (1990)).

In accordance with one aspect of the present invention, there are provided novel mature polypeptides as well as biologically active and diagnostically or therapeutically useful fragments, analogs and derivatives thereof. The receptor polypeptides of the present invention are of human origin.

In accordance with another aspect of the present invention, there are provided isolated nucleic acid molecules encoding the polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing such polypeptides by recombinant techniques comprising culturing recombinant prokaryotic and/or eukaryotic host cells, containing nucleic acid sequences encoding the polypeptides of the present invention, under conditions promoting expression of said polypeptides and subsequent recovery of said polypeptides.

In accordance with yet a further aspect of the present invention, there are provided antibodies against such polypeptides.

In accordance with another aspect of the present invention there are provided methods of screening for compounds which bind to and activate or inhibit activation of the polypeptides of the present invention.

In accordance with still another embodiment of the present invention there are provided processes of administering compounds to a host which bind to and activate the polypeptide of the present invention which are useful in the prevention and/or treatment of hypertension, epilepsy, stroke, asthma, parkinson's disease, schizophrenia, anxiety, depression and neurodegeneration.

In accordance with still another embodiment of the present invention there are provided processes of administering compounds to a host which bind to and inhibit activation of the polypeptides of the present invention which are useful in the prevention and/or treatment of migraine headaches, autoimmune diseases, cancer and graft rejection.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the cDNA sequence (SEQ ID NO:1) and deduced amino acid sequence (SEQ ID NO:2) for the putative mature $K_+$ channel 1 protein. The standard one-letter abbreviation for amino acids is used.

FIG. 2 shows the cDNA sequence and deduced amino acid sequence for the putative mature $K_+$ channel 2 protein.

FIG. 3 shows the amino acid homology between $K_+$ channel 2 protein (top) and Human DRK1 protein (bottom) (SEQ ID NO:13).

In accordance with an aspect of the present invention, there are provided isolated nucleic acids (polynucleotides) which encode for the mature $K_+$ channel 1 polypeptide having the deduced amino acid sequence of FIG. 1 (SEQ ID NO:2) or for the mature polypeptide encoded by the cDNA of the clone deposited as ATCC Deposit No. 75700 on Mar. 4, 1994.

In accordance with another aspect of the present invention, there are provided isolated nucleic acids which encode for the mature $K_+$ channel 2 polypeptide having the deduced amino acid sequence of FIG. 2 (SEQ ID NO:4) or for the mature polypeptide encoded by the cDNA of the clone deposited as ATCC Deposit No. 75830 on Jul. 15, 1994.

The ATCC numbers referred to above are directed to biological deposits with the ATCC, 12301 Parklawn Drive, Rockville, Md. 20852. Since the strains referred to are being maintained under the terms of the Budapest Treaty, each of them will be made available to a patent office signatory to the Budapest Treaty.

Polynucleotides encoding the polypeptides of the present invention may be obtained from brain, skeletal muscle and placental tissues. The polynucleotides of this invention were discovered in a cDNA library derived from human brain. They are structurally related to the K+channel gene family. $K_+$ channel 1 polypeptide contains an open reading frame encoding a polypeptide of approximately 513 amino acid residues. The polypeptide exhibits the highest degree homology to drk1 protein with approximately 40% identity and 65% similarity over a 400 amino acid stretch.

Polynucleotides encoding the $K_+$ channel 2 polypeptides of the present invention were discovered in a cDNA library derived from human brain. They are structurally related to the $K_+$ channel gene family. $K_+$ channel 2 polypeptide contains an open reading frame encoding a polypeptide of approximately 494 amino acid residues. The polypeptide exhibits the highest degree of homology to human DRK1 protein with approximately 40% identity and 66% similarity over a 488 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1 and 2 (SEQ ID NO:1 and 3) or that of the deposited clone or may be a different coding sequence which coding sequence, as a result of the redundancy or degeneracy of the genetic code, encodes the same mature polypeptide as the DNA of FIGS. 1 and 2 (SEQ ID NO:1 and 3) or the deposited cDNA.

The polynucleotide which encodes for the mature polypeptide of FIGS. 1 and 2 (SEQ ID NO:2 and 4) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1 and 2 (SEQ ID NO:2 and 4) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1 and 2 (SEQ ID NO:2 and 4) or the same mature polypeptide encoded by the cDNA of the deposited clone as well as variants of such polynucleotides which variants encode for a fragment, derivative or analog of the polypeptide of FIGS. 1 and 2 (SEQ ID NO:2 and 4) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1 and 2 (SEQ ID NO:1 and 3) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the polypeptides which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, L, et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1 and 2 (SEQ ID NO:1 and 3) or the deposited cDNA(s), i.e. function as a soluble potassium channel by retaining the ability to bind the ligands for the receptor even though the polypeptide does not function as a membrane bound potassium channel, for example, by conducting passage of ions through the cell membrane.

Alternatively, the polynucleotides may have at least 20 bases, preferably 30 bases and more preferably at least 50 bases which hybridize to a polynucleotide of the present invention and which have an identity thereto, as hereinabove described, and which may or may not retain activity. For example, such polynucleotides may be employed as probes for the polynucleotide of SEQ ID NO: 1 and 3, or for variants thereof, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and 4 as well as fragments thereof, which fragments have at least 30 bases and preferably at least 50 bases and to polypeptides encoded by such polynucleotides.

The term "gene" means the segment of DNA involved in producing a polypeptide chain; it includes regions preceding and following the coding region "leader and trailer" as well as intervening sequences (introns) between individual coding segments (exons).

Fragments of the genes may be employed as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to $K_+$ channel polypeptides which have the deduced amino acid sequences of FIGS. 1 and 2 (SEQ ID NO:2 and 4) or which have the amino acid sequence encoded by the deposited cDNA(s), as well as fragments, analogs and derivatives of such polypeptides.

The terms "fragment," "derivative" and "analog" when referring to the polypeptides of FIGS. 1 and 2 (SEQ ID NO:2 and 4) or that encoded by the deposited cDNA(s), means polypeptides which either retain essentially the same biological function or activity as such polypeptides, or retain the ability to bind the ligand of the $K_+$ channel polypeptide, however, are a soluble form of such polypeptide and, therefore, elicit no function.

The polypeptides of the present invention may be a recombinant polypeptide, a natural polypeptide or a synthetic polypeptide, preferably a recombinant polypeptide.

The fragment, derivative or analog of the polypeptides of FIGS. 1 and 2 (SEQ ID NO:2 and 4) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 and 4 (in particular the mature polypeptide) as well as polypeptides which have at least 70% similarity (preferably at least a 70% identity) to the polypeptide of SEQ ID NO:2 and 4 and more preferably at least a 90% similarity (more preferably at least a 90% identity) to the polypeptide of SEQ ID NO:2 and 4 and still more preferably at least a 95% similarity (still more preferably at least a 95% identity) to the polypeptide of SEQ ID NO:2 and 4 and also includes portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the $K^+$ channel protein genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS, HEK 293 or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The $K_+$ channel polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention relates to an assay for identifying molecules which have a modulating effect, e.g. agonist or antagonist compounds to the $K_+$ channel polypeptides of the present invention. Such an assay comprises the steps of providing an expression system that produces a functional $K_+$ channel expression product encoded by the DNA of the present invention, contacting the expression system or the product of the expression system with one or more molecules to determine its modulating effect on the bioactivity of the product and selecting from the molecules a candidate capable of modulating $K_+$ channel expression.

Agonists to the $K_+$ channel openers, including those identified by the method above, are $K_+$ channel openers, which increase $K_+$ ion flux and, therefore, are useful for treating epilepsy, stroke, hypertension, asthma, Parkinson's disease, schizophrenia, anxiety, depression and neurodegeneration. While applicant does not wish to limit the scientific reasoning behind these therapeutic uses, the high degree of localization of $K_+$ channel proteins in the brain, nervous system and myocardium, $K_+$ ion flux through the K+ channels of the present invention provides an ion balance and a concurrent therapeutic result.

Potential antagonists to the $K_+$ channel polypeptides of the present invention include an antibody against the $K^+$ channel polypeptides, or in some cases, an oligonucleotide, which bind to the $K_+$ channel polypeptides and alter its conformation such that $K_+$ ions do not pass therethrough. Soluble $K_+$ Channel polypeptides may also be used as antagonists by administering them into circulation to bind free $K_+$ ions and, therefore, reduce their concentration in vivo.

Potential antagonists also include antisense constructs produced by antisense technology. Antisense technology controls gene expression through triple-helix formation, etc. The number of $K_+$ Channels may be reduced through antisense technology, which controls gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the $K_+$ channel polypeptides. The antisense RNA oligonucleotide hybridizes to the mRNA in vivo and blocks translation of the mRNA molecule into the $K_+$ channel polypeptides (antisense—Okano, J. Neurochem., 56:560 (1991); Oligodeoxynucleotides as Antisense Inhibitors of Gene Expression, CRC Press, Boca Raton, Fla. (1988)). The antisense constructs can be delivered to cells by procedures known in the art such that the antisense RNA or DNA may be expressed in vivo.

Another example of a potential antagonist includes a small molecule which binds to and occupies the opening in the $K_+$ channel polypeptide thereby not allowing $K_+$ ions to pass therethrough, such that normal biological activity is prevented. Examples of small molecules include but are not limited to small peptides or peptide-like molecules.

A soluble form of the $K_+$ Channel polypeptides, e.g. a fragment of the polypeptides, may be employed to inhibit activation of the polypeptide by binding to the ligand to a polypeptide of the present invention and preventing the ligand from interacting with membrane bound polypepides.

The antagonist compounds which exert their effect upon the $K_+$ channel polypeptides may be employed to treat autoimmune diseases which result from abnormal cells of the immune system destroying target tissues, either by direct killing or by producing autoantibodies. In a normal immune response the n channel type of $K_+$ channel proteins are increased upwards of ten fold in normal T cells. Accordingly, the antagonists may be employed to treat autoimmune diseases such as AIDS, SLE, diabetes mellitus, multiple sclerosis and lymphocyte-mediated immune reaction against transplantation antigens.

The antagonist compounds may also be employed to treat cell-proliferative conditions, such as cancer and tumoricity, which have a similar association with immunologic factors.

The polynucleotides and polypeptides of the present invention may also be employed as research reagents and materials for discovery of treatments and diagnostics to human disease.

The antagonist or agonist compounds may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The polypeptides and agonist and antagonist compounds which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention also provides a method of detecting expression of a polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying ion channel polypeptides related to the polypeptides of the present invention. These related receptors may be identified by homology to a polypeptide of the present invention, by low stringency cross hybridization, or by identifying receptors that interact with related natural or synthetic ligands and or elicit similar behaviors after genetic or pharmacological blockade of the polypeptides of the present invention.

The present invention also contemplates the use of the genes of the present invention as a diagnostic, for example, some diseases result from inherited defective genes. These assays may be employed to diagnose autoimmune diseases and cancer. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library).

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milsrein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which my be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of $K_+$ Channel 1 Protein

The DNA sequence encoding for the $K_+$ channel 1 polypeptides of the present invention, ATCC #75700, is initially amplified using PCR oligonucleotide primers corresponding to the 5' and sequences of the processed $K^+$ channel 1 protein (minus the signal peptide sequence) and the vector sequences 3' to the $K_+$ channel protein gene. Additional nucleotides corresponding to $K_+$ channel 1 protein are added to the 5' and 3' sequences respectively. The 5' oligonucleotide primer has the sequence 5' GAC-TAAAGCTTAATGACCCTCTTACCGGG 3' (SEQ ID NO:3) contains a Hind III restriction enzyme site followed by 17 nucleotides of the coding sequence starting from the presumed terminal amino acid of the protein codon. The 3' sequence 3' GAACTTCTAGACCGCGCTCAGTCAT-TGTC 5' (SEQ ID NO:4) contains complementary sequences to an Xba I restriction enzyme site and is followed by 18 nucleotides of the non-coding sequence located 3' to the $K_+$ channel 1 protein DNA insert and to a pBluescript SK+ vector sequence located 3' to the $K_+$ channel 1 protein DNA insert. The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-9 is then digested with Hind III and Xba I. The amplified sequences are ligated into pQE-9 and are inserted in frame with the sequence encoding for the histidine tag and the RBS. The ligation mixture is then used to transform the E. coli strain M15/rep4 available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies were selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized $K_+$ channel protein is purified from this solution by chromatography on a Nickel-Chelate column under conditions that allow for tight binding by proteins containing the 6-His tag (Hochuli, E. et al., J. Chromatography 411:177–184 (1984)). $K_+$ channel 1 protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 molar sodium phosphate.

EXAMPLE 2

Cloning and expression of K+ channel 1 protein using the baculovirus expression System The DNA sequence encoding the full length K+ channel 1 protein, ATCC #75700, was amplified using PCR oligonucleotide primers corresponding to the 5' and 3' sequences of the gene:

The 5' primer has the sequence 5' CGGGATCCCTCC ATGACCCTCTTACCGGGA 3' (SEQ ID NO:5) and contains a BamH1 restriction enzyme site followed by 4 nucleotides resembling an efficient signal for the initiation of translation in eukaryotic cells (J. Mol. Biol. 1987, 196, 947–950, Kozak, M.), and just behind the first 18 nucleotides of the K+ channel 1 gene (the initiation codon for translation "ATG" is underlined). The3 ' primer has the sequence 5' CGGGATCCCGCTCAGTTATTGTCTCTGGT 3' (SEQ ID NO:6) and contains the cleavage site for the restriction endonuclease BamH1 and 18 nucleotides complementary to the 3' non-translated sequence of the K+ channel 1 gene. The amplified sequences were isolated from a 1% agarose gel using a commercially available kit ("Geneclean," BIO 101 Inc., La Jolla, Calif.). The fragment was then digested with the endonuclease BamH1 and then purified on a 1% agarose gel using a commercially available kit ("Geneclean" BIO 101 Inc., La Jolla, Calif.). This fragment is designated F2.

The vector pRG1 (modification of pVL941 vector, discussed below) is used for the expression of the K+ channel 1 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonuclease BamH1. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamH1 and then dephosphorylated using calf intestinal phosphatase by procedures known in the art. The DNA was then isolated from a 1% agarose gel and purified again on a 1% agarose gel. This vector DNA is designated V2.

Fragment F2 and the dephosphorylated plasmid V2 were ligated with T4 DNA ligase. *E. coli* HB101 cells were then transformed and bacteria identified that contained the plasmid (pBacK+ channel 1) with the K+ channel 1 gene using the enzymes BamH1. The sequence of the cloned fragment was confirmed by DNA sequencing.

5 µg of the plasmid pBacK+ channel 1 were cotransfected with 1.0 µg of a commercially available linearized baculovirus "BaculoGold™ baculovirus DNA", Pharmingen, San Diego, Calif.) using the lipofection method (Felgner et al. Proc. Natl. Acad. Sci. U.S.A., 84:7413–7417 (1987)).

1 µg of BaculoGold™ virus DNA and 5 µg of the plasmid pBacK+ channel 1 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V–K+ channel 1 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 3

Expression of Recombinant K+ channel 1 protein in COS cells

The expression of plasmid, pK+ channel 1 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire K+ channel 1 protein and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (L Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows: The DNA sequence encoding for K+ channel 1 protein, ATCC 75700, was constructed by PCR on the full-length gene cloned using two primers: the 5' primer 5' GTC-CAAGCTTGCCACCATGACCCTCTTACCCGGA 3' (SEQ ID NO:7) contains a HindIII site followed by 18 nucleotides of K+ channel 1 coding sequence starting from the initiation codon; the 3' sequence 5' CTAGCTCGAGT-CAAGCGTAGTCTGGGACGTCGTATGTAGCAGTT ATTGTCTCTGGT 3' (SEQ ID NO:8) contains complementary sequences to an XhoI site, translation stop codon, HA tag and the last 15 nucleotides of the K+ channel 1 coding sequence (not including the stop codon). Therefore, the PCR product contains a HindIII site, K+ channel 1 coding sequence followed by HA tag fused in frame, a translation termination stop codon next to the HA tag, and an Xho I site. The PCR amplified DNA fragment and the vector, pcDNAI/Amp, were digested with HindIII and XhoI restriction enzymes and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant K+ channel 1, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the K+ channel 1 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 4

Cloning and expression of K+ channel 2 protein using the baculovirus expression system The DNA sequence encoding the full length K+ channel 2 protein, ATCC #75830, was amplified using PCR oligonucleotide primers corresponding to the 5' and 3' sequences of the gene:

The 5' primer has the sequence 5' CGGGATCCCTCC ATGGACGGGTCCGGGGAG 3' (SEQ ID NO:9) and contains a BamH1 restriction enzyme site followed by 4 nucleotides resembling an efficient signal for the initiation of translation in eukaryotic cells (J. Mol. Biol. 1987, 196, 947–950, Kozak, M.), and just behind the first 18 nucleotides of the K+ channel 2 gene (the initiation codon for translation "ATG" is underlined).

The 3' primer has the sequence 5' CGGGATCCCGCT-CACTTGCAACTCTGGAG 3' (SEQ ID NO:10) and contains the cleavage site for the restriction endonuclease BamH1 and 18 nucleotides complementary to the 3' nontranslated sequence of the K+ channel 2 gene. The amplified sequences were isolated from a 1% agarose gel using a commercially available kit ("Geneclean," BIO 101 Inc., La Jolla, Calif.). The fragment was then digested with the endonuclease BamH1 and then purified again on a 1% agarose gel. This fragment is designated F2.

The vector pRG1 (modification of pVL941 vector, discussed below) is used for the expression of the K+ channel protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonuclease BamH1. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamH1 and then dephosphorylated using calf intestinal phosphatase by procedures known in the art. The DNA was then isolated from a 1% agarose gel and purified again on a 1% agarose gel. This vector DNA is designated V2.

Fragment F2 and the dephosphorylated plasmid V2 were ligated with T4 DNA ligase. *E. coli* HB101 cells were then transformed and bacteria identified that contained the plasmid (pBacK+ channel 2) with the K+ channel 2 gene using the enzymes BamH1. The sequence of the cloned fragment was confirmed by DNA sequencing.

5 µg of the plasmid pBacK+ channel 2 were cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. U.S.A., 84:7413–7417 (1987)). 1 µg of BaculoGold™ virus DNA and 5 µg of the plasmid pBacK+ channel 2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V–K+ channel 2 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 5

Expression of Recombinant K+ channel 2 protein in COS cells

The expression of plasmid, pK+ channel 2 HA is derived from a vector pcDNAI/Amp (Invitrogen) containing: 1)

SV40 origin of replication, 2) ampicillin resistance gene, 3) E. coli replication origin, 4) CMV promoter followed by a polylinker region, a SV40 intron and polyadenylation site. A DNA fragment encoding the entire K+ channel 2 protein and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A. Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for K+ channel 2 protein, ATCC #75830, was constructed by PCR on the full-length gene cloned using two primers: the 5' primer 5' GTC-CAAGCTTGCCACCATGGACGGGTCCGGGGAG 3' (SEQ ID NO:11) contains a HindIII site followed by 18 nucleotides of K+ channel 2 coding sequence starting from the initiation codon; the 3' sequence 5 ' CTAGCTCGAGT-CAAGCGTAGTCTGGGACGTCGTATGGG-TAGCACTTGCAACTCTGGAGCCG 3' (SEQ ID NO:12) contains complementary sequences to an XhoI site, translation stop codon, HA tag and the last 18 nucleotides of the K+ channel 2 coding sequence (not including the stop codon). Therefore, the PCR product contains a HindIII site, K+ channel 2 coding sequence followed by HA tag fused in frame, a translation termination stop codon next to the HA tag, and an Xho I site. The PCR amplified DNA fragment and the vector, pcDNAI/Amp, were digested with HindIII and XhoI restriction enzymes and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant K+ channel 2, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the K+ channel 2 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

Numerous modifications and variations of the present invention are possible in light of the above teachings and, therefore, within the scope of the appended claims, the invention may be practiced otherwise than as particularly described.

What is claimed is:

1. An isolated polypetide comprising:

a polypeptide having an amino acid sequence encoded by a polynucleotide which is at least 95% identical to a polynucleotide selected from the group consisting of:
   (a) a polynucleotide encoding a polypeptide having the amino acid sequence of SEQ ID No. 2; and
   (b) a polynucleotide encoding a polypeptide having the amino acid sequence of SEQ ID NO:4, wherein said polypeptide has substantially the same biologically functional activity of the polypeptide comprising the nucleic acid sequence as forth in (a) or (b).

2. An isolated polypeptide comprising:

a polypeptide sequence encoded by a polynucleotide which is at least 95% identical to a member selected from the group consisting of:
   (a) a polynucleotide encoding a K$^+$ channel polypeptide having the amino acid sequence encoded by the human cDNA contained in ATCC Deposit No. 75700; and
   (b) a polynucleotide encoding a K$^+$ channel polypeptide having the amino acid sequence encoded by the human cDNA contained in ATCC Deposit No. 75830, wherein said polypetide has substantially the same biologically functional activity of the polypeptide comprising the nucleic acid sequence as set forth in (a) or (b).

3. The isolated polypeptide of claim 1, comprising the polypeptide sequence of SEQ ID NO:2.

4. The isolated polypeptide of claim 1, comprising the polypeptide sequence of SEQ ID NO:4.

5. The isolated polypeptide of claim 2 comprising the mature polypeptide encoded by the human cDNA in ATCC Deposit No. 75700.

6. The isolated polypeptide of claim 2 comprising the mature polypeptide encoded by the human cDNA in ATCC Deposit No. 75830.

7. An isolated polypeptide produced from a host cell transformed with a polynucleotide, comprising a polynucleotide sequence which is at least 95% identical to a member selected from the group consisting of:
   (i) a polynucleotide encoding the amino acid sequence of SEQ ID NO:2; and
   (ii) a polynucleotide encoding the amino acid sequence of SEQ ID NO:4, wherein said polypeptide has substantially the same biologically functional activity of the polypeptide comprising the nucleic acid sequence as forth in (i) or (ii).

8. An isolated polypeptide according to claim 7, wherein the host cell is transformed with a polynucleotide having a polynucleotide sequence according to SEQ ID NO: 1.

9. An isolated polypeptide according to claim 7, wherein the host cell is transformed with a polynucleotide having a polynucleotide sequence according to SEQ ID NO: 3.

10. An isolated polypeptide according to claim 7, wherein the host cell is transformed with a polynucleotide which is identical to a polynucleotide encoding the polypeptide of SEQ ID NO:2.

11. An isolated polypeptide according to claim 7, wherein the host cell is transformed with a polynucleotide which is identical to a polynucleotide encoding the polypeptide of SEQ ID NO:4.

12. An isolated polypeptide produced from a host cell transformed with a polynucleotide, comprising a polynucleotide sequence which is at least 95% identical to a member selected from the group consisting of:

(i) a polynucleotide encoding the same mature $K^+$ channel polypeptide encoded by the human cDNA of ATCC Deposit No. 75700; and (ii) a polynucleotide encoding the same mature $K^+$ channel polypeptide encoded by the human cDNA of ATCC Deposit No. 75830, wherein said polypeptide has substantially the same biologically functional activity of the polypeptide comprising the nucleic acid sequence as set forth in (i) or (ii).

13. An isolated polypeptide according to claim 12, wherein the host cell is transformed with a polynucleotide encoding a polypeptide identical to the polypeptide encoded by the human cDNA of ATCC Deposit No. 75700.

14. An isolated polypeptide according to claim 12, wherein the host cell is transformed with a polynucleotide encoding a polypeptide identical to the polypeptide encoded by the human cDNA of ATCC Deposit No. 75830.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 2127 BASE PAIRS
( B ) TYPE: NUCLEIC ACID
( C ) STRANDEDNESS: SINGLE
( D ) TOPOLOGY: LINEAR ( i i ) MOLECULE TYPE: cDNA ( x i ) SEQUENCE DESCRIPTION: SEQ ID NO:1:

```
ACAAAAGCTG  GAGCTCCACC  GCGGTGCGGC  CGCTCTAGAA  CTAGTGGATC  CCCCGGGCTG    60

CAGGGGCTCC  GAGGGCGGGA  GCTGAGCCGG  GCCCCGGGAC  CGAAGTTTGG  CGGCGGCTCC   120

GGGAGGCAGA  GCGGGCTCCC  CGGGCGACTT  CCAGGCCCCT  CTCGCGTCCT  CGCCCCGGAC   180

CCGTGGGCAG  TCGGGGGGGA  CGGAAGCCGC  GGCCGGGCCA  ACTCCGAGGC  GGGGACGCCG   240

CGACGGGAAC  TTGAGGCCCG  AGAGGGATGT  GAAGGCCCAA  A  ATG  ACC  CTC  TTA  CCG   296
                                                 Met  Thr  Leu  Leu  Pro
                                                                        5

GGA  GAC  AAT  TCT  GAC  TAC  GAC  TAC  AGC  GCG  CTG  AGC  TGC  ACC  TCG  GAC    344
Gly  Asp  Asn  Ser  Asp  Tyr  Asp  Tyr  Ser  Ala  Leu  Ser  Cys  Thr  Ser  Asp
              10                        15                        20

GCC  TCC  TTC  CAC  CCG  GCC  TTC  CTC  CCG  CAG  CGC  CAG  GCC  ATC  AAG  GGC    392
Ala  Ser  Phe  His  Pro  Ala  Phe  Leu  Pro  Gln  Arg  Gln  Ala  Ile  Lys  Gly
              25                        30                        35

GCG  TTC  TAC  CGC  CGG  GCG  CAG  CGG  CTG  CGG  CCG  CAG  GAT  GAG  CCC  CGC    440
Ala  Phe  Tyr  Arg  Arg  Ala  Gln  Arg  Leu  Arg  Pro  Gln  Asp  Glu  Pro  Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 40  |     |     |     |     | 45  |     |     |     |     | 50  |     |     |      |
| CAG | GGC | TGT | CAG | CCC | GAG | GAC | CGC | CGC | CGT | CGG | ATC | ATC | ATC | AAC | GTA | 488  |
| Gln | Gly | Cys | Gln | Pro | Glu | Asp | Arg | Arg | Arg | Arg | Ile | Ile | Ile | Asn | Val |      |
|     |     | 55  |     |     |     | 60  |     |     |     |     | 65  |     |     |     |     |      |
| GGC | GGC | ATC | AAG | TAC | TCG | CTG | CCC | TGG | ACC | ACG | CTG | GAC | GAG | TTC | CCG | 536  |
| Gly | Gly | Ile | Lys | Tyr | Ser | Leu | Pro | Trp | Thr | Thr | Leu | Asp | Glu | Phe | Pro |      |
| 70  |     |     |     |     | 75  |     |     |     |     | 80  |     |     |     |     | 85  |      |
| CTG | ACG | CGC | CTG | GGC | CAG | CTC | AAG | GCC | TGC | ACC | AAC | TTC | GAC | GAC | ATC | 584  |
| Leu | Thr | Arg | Leu | Gly | Gln | Leu | Lys | Ala | Cys | Thr | Asn | Phe | Asp | Asp | Ile |      |
|     |     |     |     | 90  |     |     |     |     | 95  |     |     |     |     | 100 |     |      |
| CTC | AAC | GTG | TGC | GAT | GAC | TAC | GAC | GTC | ACC | TGC | AAC | GAG | TTC | TTC | TTC | 632  |
| Leu | Asn | Val | Cys | Asp | Asp | Tyr | Asp | Val | Thr | Cys | Asn | Glu | Phe | Phe | Phe |      |
|     |     |     | 105 |     |     |     |     | 110 |     |     |     |     | 115 |     |     |      |
| GAC | CGC | AAC | CCG | GGG | GCC | TTC | GGC | ACT | ATC | CTG | ACC | TTC | CTG | CGC | GCG | 680  |
| Asp | Arg | Asn | Pro | Gly | Ala | Phe | Gly | Thr | Ile | Leu | Thr | Phe | Leu | Arg | Ala |      |
|     |     | 120 |     |     |     |     | 125 |     |     |     |     | 130 |     |     |     |      |
| GGC | AAG | CTG | CGG | CTG | CTG | CGC | GAG | ATG | TGC | GCG | CTG | TCC | TTC | CAG | GAG | 728  |
| Gly | Lys | Leu | Arg | Leu | Leu | Arg | Glu | Met | Cys | Ala | Leu | Ser | Phe | Gln | Glu |      |
|     | 135 |     |     |     |     | 140 |     |     |     |     | 145 |     |     |     |     |      |
| GAG | CTG | CTG | TAC | TGG | GGC | ATC | GCG | GAG | GAC | CAC | CTG | GAC | GGC | TGC | TGC | 776  |
| Glu | Leu | Leu | Tyr | Trp | Gly | Ile | Ala | Glu | Asp | His | Leu | Asp | Gly | Cys | Cys |      |
| 150 |     |     |     |     | 155 |     |     |     |     | 160 |     |     |     |     | 165 |      |
| AAG | CGC | CGC | TAC | CTG | CAG | AAG | ATT | GAG | GAG | TTC | GCG | GAG | ATG | GTG | GAG | 824  |
| Lys | Arg | Arg | Tyr | Leu | Gln | Lys | Ile | Glu | Glu | Phe | Ala | Glu | Met | Val | Glu |      |
|     |     |     |     | 170 |     |     |     |     | 175 |     |     |     |     | 180 |     |      |
| CGG | GAG | GAA | GAG | GAC | GAC | GCG | CTG | GAC | AGC | GAG | GGC | CGC | GAC | AGC | GAG | 872  |
| Arg | Glu | Glu | Glu | Asp | Asp | Ala | Leu | Asp | Ser | Glu | Gly | Arg | Asp | Ser | Glu |      |
|     |     |     | 185 |     |     |     |     | 190 |     |     |     |     | 195 |     |     |      |
| GGC | CCG | GCC | GAG | GGC | GAG | GGC | CGC | CTG | GGG | CGC | TGC | ATG | CGG | CGA | CTG | 920  |
| Gly | Pro | Ala | Glu | Gly | Glu | Gly | Arg | Leu | Gly | Arg | Cys | Met | Arg | Arg | Leu |      |
|     |     | 200 |     |     |     |     | 205 |     |     |     |     | 210 |     |     |     |      |
| CGC | GAC | ATG | GTG | GAG | AGG | CCG | CAC | TCG | GGG | CTG | CCT | GGC | AAG | GTG | TTC | 968  |
| Arg | Asp | Met | Val | Glu | Arg | Pro | His | Ser | Gly | Leu | Pro | Gly | Lys | Val | Phe |      |
|     | 215 |     |     |     |     | 220 |     |     |     |     | 225 |     |     |     |     |      |
| GCC | TGC | CTG | TCG | GTG | CTC | TTC | GTG | ACC | GTC | ACC | GCC | GTC | AAC | CTC | TCC | 1016 |
| Ala | Cys | Leu | Ser | Val | Leu | Phe | Val | Thr | Val | Thr | Ala | Val | Asn | Leu | Ser |      |
| 230 |     |     |     |     | 235 |     |     |     |     | 240 |     |     |     |     | 245 |      |
| GTC | AGC | ACC | TTG | CCC | AGC | CTG | AGG | GAG | GAG | GAG | GAG | CAG | GGC | CAC | TGT | 1064 |
| Val | Ser | Thr | Leu | Pro | Ser | Leu | Arg | Glu | Glu | Glu | Glu | Gln | Gly | His | Cys |      |
|     |     |     |     | 250 |     |     |     |     | 255 |     |     |     |     | 260 |     |      |
| TCC | CAG | ATG | TGC | CAC | AAC | GTC | TTC | ATC | GTG | GAG | TCG | GTG | TGC | GTG | GGC | 1112 |
| Ser | Gln | Met | Cys | His | Asn | Val | Phe | Ile | Val | Glu | Ser | Val | Cys | Val | Gly |      |
|     |     |     | 265 |     |     |     |     | 270 |     |     |     |     | 275 |     |     |      |
| TGG | TTC | TCC | CTG | GAG | TTC | CTC | CTG | CGG | CTC | ATT | CAG | GCG | CCC | AGC | AAG | 1160 |
| Trp | Phe | Ser | Leu | Glu | Phe | Leu | Leu | Arg | Leu | Ile | Gln | Ala | Pro | Ser | Lys |      |
|     |     | 280 |     |     |     |     | 285 |     |     |     |     | 290 |     |     |     |      |
| TTC | GCC | TTC | CTG | CGG | AGC | CCG | CTG | ACG | CTG | ATC | GAC | CTG | GTG | GCC | ATC | 1208 |
| Phe | Ala | Phe | Leu | Arg | Ser | Pro | Leu | Thr | Leu | Ile | Asp | Leu | Val | Ala | Ile |      |
|     | 295 |     |     |     |     | 300 |     |     |     |     | 305 |     |     |     |     |      |
| CTG | CCC | TAC | TAC | ATC | ACG | CTG | CTG | GTG | GAC | GGC | GCC | GCC | GCA | GGC | CGT | 1256 |
| Leu | Pro | Tyr | Tyr | Ile | Thr | Leu | Leu | Val | Asp | Gly | Ala | Ala | Ala | Gly | Arg |      |
| 310 |     |     |     |     | 315 |     |     |     |     | 320 |     |     |     |     | 325 |      |
| CGC | AAG | CCC | GGC | GCG | GGC | AAC | AGC | TAC | CTG | GAC | AAG | GTG | GGG | CTG | GTG | 1304 |
| Arg | Lys | Pro | Gly | Ala | Gly | Asn | Ser | Tyr | Leu | Asp | Lys | Val | Gly | Leu | Val |      |
|     |     |     |     | 330 |     |     |     |     | 335 |     |     |     |     | 340 |     |      |
| CTG | CGC | GTG | CTG | CGG | GCG | CTG | CGC | ATC | CTG | TAC | GTG | ATG | CGC | CTG | GCG | 1352 |
| Leu | Arg | Val | Leu | Arg | Ala | Leu | Arg | Ile | Leu | Tyr | Val | Met | Arg | Leu | Ala |      |
|     |     |     | 345 |     |     |     |     | 350 |     |     |     |     | 355 |     |     |      |
| CGC | CAC | TCC | CTG | GGG | CTG | CAG | ACG | CTG | GGG | CTC | ACG | GCC | CGC | CGC | TGC | 1400 |
| Arg | His | Ser | Leu | Gly | Leu | Gln | Thr | Leu | Gly | Leu | Thr | Ala | Arg | Arg | Cys |      |

| | | | | | | | | | | | | | | | | |
|---|---|---|---|---|---|---|---|---|---|---|---|---|---|---|---|---|
| ACC | CGC | GAG | TTC | GGG | CTC | CTG | CTG | CTC | TTC | CTC | TGC | GTG | GCC | ATC | GCC | 1448 |
| Thr | Arg | Glu | Phe | Gly | Leu | Leu | Leu | Leu | Phe | Leu | Cys | Val | Ala | Ile | Ala | |
| | 375 | | | | 380 | | | | | 385 | | | | | | |
| CTC | TTC | GCG | CCC | CTG | CTC | TAC | GTC | ATC | GAG | AAC | GAG | ATG | GCC | GAC | AGC | 1496 |
| Leu | Phe | Ala | Pro | Leu | Leu | Tyr | Val | Ile | Glu | Asn | Glu | Met | Ala | Asp | Ser | |
| 390 | | | | | 395 | | | | 400 | | | | | 405 | | |
| CCC | GAG | TTC | ACC | AGC | ATC | CCT | GCC | TGC | TAC | TGG | TGG | GCT | GTC | ATC | ACC | 1544 |
| Pro | Glu | Phe | Thr | Ser | Ile | Pro | Ala | Cys | Tyr | Trp | Trp | Ala | Val | Ile | Thr | |
| | | | | 410 | | | | | 415 | | | | | 420 | | |
| ATG | ACG | ACG | GTG | GAC | TAT | GGC | GAC | ATG | GTC | CCC | AGG | AGC | ACC | CCG | GGC | 1592 |
| Met | Thr | Thr | Val | Asp | Tyr | Gly | Asp | Met | Val | Pro | Arg | Ser | Thr | Pro | Gly | |
| | | | 425 | | | | | 430 | | | | | 435 | | | |
| CAG | GTA | GTG | GCC | CTG | AGC | AGC | ATC | CTG | AGC | GGC | ATC | CTG | CTC | ATG | GCC | 1640 |
| Gln | Val | Val | Ala | Leu | Ser | Ser | Ile | Leu | Ser | Gly | Ile | Leu | Leu | Met | Ala | |
| | | 440 | | | | | 445 | | | | | 450 | | | | |
| TTC | CCA | GTC | ACC | TCC | ATC | TTC | CAC | ACC | TTC | TCC | CCC | TCC | TAC | CTG | GAG | 1688 |
| Phe | Pro | Val | Thr | Ser | Ile | Phe | His | Thr | Phe | Ser | Pro | Ser | Tyr | Leu | Glu | |
| | 455 | | | | | 460 | | | | | 465 | | | | | |
| CTC | AAA | CAG | GAG | CAA | GAG | AGG | GTG | ATG | TTC | CGG | AGG | GCG | CAG | TTC | CTC | 1736 |
| Leu | Lys | Gln | Glu | Gln | Glu | Arg | Val | Met | Phe | Arg | Arg | Ala | Gln | Phe | Leu | |
| 470 | | | | | 475 | | | | | 480 | | | | | 485 | |
| ATC | AAA | ACC | AAG | TCG | CAG | CTG | AGC | GTG | TCC | CAG | GAC | AGT | GAC | ATC | TTG | 1784 |
| Ile | Lys | Thr | Lys | Ser | Gln | Leu | Ser | Val | Ser | Gln | Asp | Ser | Asp | Ile | Leu | |
| | | | | 490 | | | | | 495 | | | | | 500 | | |
| TTC | GGA | AGT | GCC | TCC | TCG | GAC | ACC | AGA | GAC | AAT | AAC | TGAGCGCGGA | | | | 1830 |
| Phe | Gly | Ser | Ala | Ser | Ser | Asp | Thr | Arg | Asp | Asn | Asn | | | | | |
| | | | 505 | | | | | 510 | | | | | | | | |

```
GGACACGCCT GCCCTGCCTG CCATCTGTGG CCCGAAGCCA TTGCCATCCA CTGCAGACGC 1890
CTGGAGAGGG ACAGGCCGCT TCCGAGTGCA GTCCTGGCGC AGCACCGACT CCCACGCACC 1950
CGGGGAAGGA CACCCTCACT CCCACACCCC GGGAAGAACA CTAGAACATC AGCAGAGGGG 2010
CCCTGCCCCT CCGCCTGCAG CCGTGAAAGG AAGCTGGGTC ATCAGCCCAG CCCCGCCCAC 2070
CCCAGCCCCT ATGTGTGTTT CCCTCAATAA GGAGATGCCT TGTTCTTTC ACCATGC    2127
```

( 2 ) INFORMATION FOR SEQ ID NO:2:

( i ) SEQUENCE CHARACTERISTICS:
        ( A ) LENGTH: 513 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

| | | | | | | | | | | | | | | |
|---|---|---|---|---|---|---|---|---|---|---|---|---|---|---|
| Met | Thr | Leu | Leu | Pro | Gly | Asp | Asn | Ser | Asp | Tyr | Asp | Tyr | Ser | Ala |
| | | | | 5 | | | | 10 | | | | | | 15 |
| Leu | Ser | Cys | Thr | Ser | Asp | Ala | Ser | Phe | His | Pro | Ala | Phe | Leu | Pro |
| | | | | 20 | | | | 25 | | | | | | 30 |
| Gln | Arg | Gln | Ala | Ile | Lys | Gly | Ala | Phe | Tyr | Arg | Arg | Ala | Gln | Arg |
| | | | | 35 | | | | 40 | | | | | | 45 |
| Leu | Arg | Pro | Gln | Asp | Glu | Pro | Arg | Gln | Gly | Cys | Gln | Pro | Glu | Asp |
| | | | | 50 | | | | 55 | | | | | | 60 |
| Arg | Arg | Arg | Arg | Ile | Ile | Ile | Asn | Val | Gly | Gly | Ile | Lys | Tyr | Ser |
| | | | | 65 | | | | 70 | | | | | | 75 |
| Leu | Pro | Trp | Thr | Thr | Leu | Asp | Glu | Phe | Pro | Leu | Thr | Arg | Leu | Gly |
| | | | | 80 | | | | 85 | | | | | | 90 |
| Gln | Leu | Lys | Ala | Cys | Thr | Asn | Phe | Asp | Asp | Ile | Leu | Asn | Val | Cys |

|   |   |   |   | 95 |   |   |   |   | 100 |   |   |   |   | 105 |
|---|---|---|---|---|---|---|---|---|---|---|---|---|---|---|
| Asp | Asp | Tyr | Asp | Val | Thr | Cys | Asn | Glu | Phe | Phe | Asp | Arg | Asn |
|   |   |   |   | 110 |   |   |   |   | 115 |   |   |   |   | 120 |
| Pro | Gly | Ala | Phe | Gly | Thr | Ile | Leu | Thr | Phe | Leu | Arg | Ala | Gly | Lys |
|   |   |   |   | 125 |   |   |   |   | 130 |   |   |   |   | 135 |
| Leu | Arg | Leu | Leu | Arg | Glu | Met | Cys | Ala | Leu | Ser | Phe | Gln | Glu | Glu |
|   |   |   |   | 140 |   |   |   |   | 145 |   |   |   |   | 150 |
| Leu | Leu | Tyr | Trp | Gly | Ile | Ala | Glu | Asp | His | Leu | Asp | Gly | Cys | Cys |
|   |   |   |   | 155 |   |   |   |   | 160 |   |   |   |   | 165 |
| Lys | Arg | Arg | Tyr | Leu | Gln | Lys | Ile | Glu | Glu | Phe | Ala | Glu | Met | Val |
|   |   |   |   | 170 |   |   |   |   | 175 |   |   |   |   | 180 |
| Glu | Arg | Glu | Glu | Glu | Asp | Asp | Ala | Leu | Asp | Ser | Glu | Gly | Arg | Asp |
|   |   |   |   | 185 |   |   |   |   | 190 |   |   |   |   | 195 |
| Ser | Glu | Gly | Pro | Ala | Glu | Gly | Glu | Gly | Arg | Leu | Gly | Arg | Cys | Met |
|   |   |   |   | 200 |   |   |   |   | 205 |   |   |   |   | 210 |
| Arg | Arg | Leu | Arg | Asp | Met | Val | Glu | Arg | Pro | His | Ser | Gly | Leu | Pro |
|   |   |   |   | 215 |   |   |   |   | 220 |   |   |   |   | 225 |
| Gly | Lys | Val | Phe | Ala | Cys | Leu | Ser | Val | Leu | Phe | Val | Thr | Val | Thr |
|   |   |   |   | 230 |   |   |   |   | 235 |   |   |   |   | 240 |
| Ala | Val | Asn | Leu | Ser | Val | Ser | Thr | Leu | Pro | Ser | Leu | Arg | Glu | Glu |
|   |   |   |   | 245 |   |   |   |   | 250 |   |   |   |   | 255 |
| Glu | Glu | Gln | Gly | His | Cys | Ser | Gln | Met | Cys | His | Asn | Val | Phe | Ile |
|   |   |   |   | 260 |   |   |   |   | 265 |   |   |   |   | 270 |
| Val | Glu | Ser | Val | Cys | Val | Gly | Trp | Phe | Ser | Leu | Glu | Phe | Leu | Leu |
|   |   |   |   | 275 |   |   |   |   | 280 |   |   |   |   | 285 |
| Arg | Leu | Ile | Gln | Ala | Pro | Ser | Lys | Phe | Ala | Phe | Leu | Arg | Ser | Pro |
|   |   |   |   | 290 |   |   |   |   | 295 |   |   |   |   | 300 |
| Leu | Thr | Leu | Ile | Asp | Leu | Val | Ala | Ile | Leu | Pro | Tyr | Tyr | Ile | Thr |
|   |   |   |   | 305 |   |   |   |   | 310 |   |   |   |   | 315 |
| Leu | Leu | Val | Asp | Gly | Ala | Ala | Ala | Gly | Arg | Arg | Lys | Pro | Gly | Ala |
|   |   |   |   | 320 |   |   |   |   | 325 |   |   |   |   | 330 |
| Gly | Asn | Ser | Tyr | Leu | Asp | Lys | Val | Gly | Leu | Val | Leu | Arg | Val | Leu |
|   |   |   |   | 335 |   |   |   |   | 340 |   |   |   |   | 345 |
| Arg | Ala | Leu | Arg | Ile | Leu | Tyr | Val | Met | Arg | Leu | Ala | Arg | His | Ser |
|   |   |   |   | 350 |   |   |   |   | 355 |   |   |   |   | 360 |
| Leu | Gly | Leu | Gln | Thr | Leu | Gly | Leu | Thr | Ala | Arg | Arg | Cys | Thr | Arg |
|   |   |   |   | 365 |   |   |   |   | 370 |   |   |   |   | 375 |
| Glu | Phe | Gly | Leu | Leu | Leu | Leu | Phe | Leu | Cys | Val | Ala | Ile | Ala | Leu |
|   |   |   |   | 380 |   |   |   |   | 385 |   |   |   |   | 390 |
| Phe | Ala | Pro | Leu | Leu | Tyr | Val | Ile | Glu | Asn | Glu | Met | Ala | Asp | Ser |
|   |   |   |   | 395 |   |   |   |   | 400 |   |   |   |   | 405 |
| Pro | Glu | Phe | Thr | Ser | Ile | Pro | Ala | Cys | Tyr | Trp | Trp | Ala | Val | Ile |
|   |   |   |   | 410 |   |   |   |   | 415 |   |   |   |   | 420 |
| Thr | Met | Thr | Thr | Val | Asp | Tyr | Gly | Asp | Met | Val | Pro | Arg | Ser | Thr |
|   |   |   |   | 425 |   |   |   |   | 430 |   |   |   |   | 435 |
| Pro | Gly | Gln | Val | Val | Ala | Leu | Ser | Ser | Ile | Leu | Ser | Gly | Ile | Leu |
|   |   |   |   | 440 |   |   |   |   | 445 |   |   |   |   | 450 |
| Leu | Met | Ala | Phe | Pro | Val | Thr | Ser | Ile | Phe | His | Thr | Phe | Ser | Pro |
|   |   |   |   | 455 |   |   |   |   | 460 |   |   |   |   | 465 |
| Ser | Tyr | Leu | Glu | Leu | Lys | Gln | Glu | Gln | Glu | Arg | Val | Met | Phe | Arg |
|   |   |   |   | 470 |   |   |   |   | 475 |   |   |   |   | 480 |
| Arg | Ala | Gln | Phe | Leu | Ile | Lys | Thr | Lys | Ser | Gln | Leu | Ser | Val | Ser |
|   |   |   |   | 485 |   |   |   |   | 490 |   |   |   |   | 495 |

| | | | | | | | | | | | | | | |
|---|---|---|---|---|---|---|---|---|---|---|---|---|---|---|
|Gln|Asp|Ser|Asp|Ile|Leu|Phe|Gly|Ser|Ala|Ser|Ser|Asp|Thr|Arg|
| | | |500| | | | |505| | | |510| | |

Asp Asn Asn ( 2 ) INFORMATION FOR SEQ ID NO:3:

( i ) SEQUENCE CHARACTERISTICS:
        ( A ) LENGTH: 2483 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:3:

| | | | | | |
|---|---|---|---|---|---|
|GGTCGCAACC|CCTCGGTGAC|CCGCTGCGCC|CGAGGAGGGG|CCGGCGGTGC|GCGGTGGTGG|60|
|CGGCGGGCGC|GGCAGCTGTG|CCCGTCTGCC|CAAGGGTTAA|TCCGTCCCCT|GCAGCTGCCG|120|
|CGCGTGCCTT|GCAGAATTTC|ACCAGAAGAG|GGTACAGTTT|GAAAAGCTCC|TGACGTCAGG|180|
|CTGGAATTCC|TATTGTGTTT|AGAAAAGGCT|CGGGCAAAGC|CAGCCCAAGT|TCGCTCTCTG|240|
|CACACCTCGA|GCACCTCGCG|GACGGCGTGG|GTCCGCCAGC|TCCGGGACCT|GCCGCCGCTG|300|
|CCTGCGCGCC|CCGGGGCGGA|GGACGGTGCC|AGCCGCCCAC|GAGGAGACCC|CGCTCCCGCA|360|
|GGAGGCCGAG|CTGAAGCGGC|GGAGCGCGCC|GCCAGCCAGC|CGGGGTGAGT|GCCCCGGGCG|420|
|AGGCCGGCGG|CCGCCAAAGC|CCCCGCGGGT|TCGTCCGGGC|GCCCGGATGC|CAGCCCCGAG|480|
|CCCCGCCGCC|GGGTGCATGC|CTCCCCCGCG|GCGCGCCCCC|GCAGGCTGCT|GCCCGCTGTG|540|
|ACCGCCCTTC|CCCGCAGGCG|GGCGCCGGCC|AGGCTCTCCC|ACGAGATACG|ACGCACGGGT|600|
|GGCACCCGCC|GGACCCCCAA|CGACAACGGC|GGCGACGTCT|GCAGGGGGCG|CGGGGCGGAG|660|
|CCTGCGAGGG|CGCGCACGGG|GAGG|||||

| | | | | | | | | | | | | | | | | |
|---|---|---|---|---|---|---|---|---|---|---|---|---|---|---|---|---|
| | | | |ATG|GAC|GGG|TCC|GGG|GAG|CGC|AGC|CTC|CCG| | | |714|
| | | | |Met|Asp|Gly|Ser|Gly|Glu|Arg|Ser|Leu|Pro| | | |
| | | | |1| | |5| | | | |10| | | | |

| | | | | | | | | | | | | | | |
|---|---|---|---|---|---|---|---|---|---|---|---|---|---|---|
|GAG|CCG|GGC|AGC|CAG|AGC|TCC|GCT|GCC|AGC|GAC|GAC|ATA|GAG|ATA|GTC|762|
|Glu|Pro|Gly|Ser|Gln|Ser|Ser|Ala|Ala|Ser|Asp|Asp|Ile|Glu|Ile|Val|
| | | |15| | | | |20| | | | |25| | |

| | | | | | | | | | | | | | | |
|---|---|---|---|---|---|---|---|---|---|---|---|---|---|---|
|GTC|AAC|GTG|GGG|GGC|GTG|CGG|CAG|GTG|CTG|TAC|GGG|GAC|CTC|CTC|AGT|810|
|Val|Asn|Val|Gly|Gly|Val|Arg|Gln|Val|Leu|Tyr|Gly|Asp|Leu|Leu|Ser|
| | | |30| | | | |35| | | | |40| | |

| | | | | | | | | | | | | | | |
|---|---|---|---|---|---|---|---|---|---|---|---|---|---|---|
|CAG|TAC|CCT|GAG|ACC|CGG|CTG|GCG|GAG|CTC|ATC|AAC|TGC|TTG|GCT|GGG|858|
|Gln|Tyr|Pro|Glu|Thr|Arg|Leu|Ala|Glu|Leu|Ile|Asn|Cys|Leu|Ala|Gly|
| | | |45| | | | |50| | | | |55| | |

| | | | | | | | | | | | | | | |
|---|---|---|---|---|---|---|---|---|---|---|---|---|---|---|
|GGC|TAC|GAC|ACC|ATC|TTC|TCC|CTG|TGC|GAC|GAC|TAC|GAC|CCC|GGC|AAG|906|
|Gly|Tyr|Asp|Thr|Ile|Phe|Ser|Leu|Cys|Asp|Asp|Tyr|Asp|Pro|Gly|Lys|
| | | |60| | | | |65| | | | |70| | |

| | | | | | | | | | | | | | | |
|---|---|---|---|---|---|---|---|---|---|---|---|---|---|---|
|CGC|GAG|TTC|TAC|TTT|GAC|AGG|GAC|CCG|GAC|GCC|TTC|AAG|TGT|GTC|ATC|954|
|Arg|Glu|Phe|Tyr|Phe|Asp|Arg|Asp|Pro|Asp|Ala|Phe|Lys|Cys|Val|Ile|
|75| | | |80| | | | |85| | | | |90| |

| | | | | | | | | | | | | | | |
|---|---|---|---|---|---|---|---|---|---|---|---|---|---|---|
|GAG|GTG|TAC|TAT|TTC|GGG|GAG|GTC|CAC|ATG|AAG|AAG|GGC|ATC|TGC|CCC|1002|
|Glu|Val|Tyr|Tyr|Phe|Gly|Glu|Val|His|Met|Lys|Lys|Gly|Ile|Cys|Pro|
| | | |95| | | | |100| | | | |105| | |

| | | | | | | | | | | | | | | |
|---|---|---|---|---|---|---|---|---|---|---|---|---|---|---|
|ATC|TGC|TTC|AAG|AAC|GAG|ATG|GAC|TTC|TGG|AAG|GTG|GAC|CTC|AAG|TTC|1050|
|Ile|Cys|Phe|Lys|Asn|Glu|Met|Asp|Phe|Trp|Lys|Val|Asp|Leu|Lys|Phe|
| | |110| | | | |115| | | | |120| | | |

| | | | | | | | | | | | | | | |
|---|---|---|---|---|---|---|---|---|---|---|---|---|---|---|
|CTG|GAC|GAC|TGT|TGC|AAG|AGC|CAC|CTG|AGC|GAG|AAG|CGC|GAG|GAG|CTG|1098|
|Leu|Asp|Asp|Cys|Cys|Lys|Ser|His|Leu|Ser|Glu|Lys|Arg|Glu|Glu|Leu|
| | |125| | | | |130| | | | |135| | | |

| | | | | | | | | | | | | | | |
|---|---|---|---|---|---|---|---|---|---|---|---|---|---|---|
|GAG|GAG|ATC|GCG|CGC|CGC|GTG|CAG|CTC|ATC|CTG|GAC|GAC|CTG|GGC|GTG|1146|
|Glu|Glu|Ile|Ala|Arg|Arg|Val|Gln|Leu|Ile|Leu|Asp|Asp|Leu|Gly|Val|
| | |140| | | | |145| | | | |150| | | |

-continued

| | | | | | | | | | | | | | | | | |
|---|---|---|---|---|---|---|---|---|---|---|---|---|---|---|---|---|
| GAC | GCG | GCC | GAG | GGC | CGC | TGG | CGC | CGC | TGC | CAG | AAG | TGC | GTC | TGG | AAG | 1194 |
| Asp | Ala | Ala | Glu | Gly | Arg | Trp | Arg | Arg | Cys | Gln | Lys | Cys | Val | Trp | Lys | |
| 155 | | | | 160 | | | | | 165 | | | | | | 170 | |
| TTC | CTG | GAG | AAG | CCC | GAG | TCG | TCG | TGC | CCG | GCG | CGG | GTG | GTG | GCC | GAG | 1242 |
| Phe | Leu | Glu | Lys | Pro | Glu | Ser | Ser | Cys | Pro | Ala | Arg | Val | Val | Ala | Glu | |
| | | | | 175 | | | | | 180 | | | | | | 185 | |
| CTC | TCC | TTC | CTG | CTC | ATC | CTC | GTC | TCG | TCC | GTG | GTC | ATG | TGC | ATG | GAC | 1290 |
| Leu | Ser | Phe | Leu | Leu | Ile | Leu | Val | Ser | Ser | Val | Val | Met | Cys | Met | Asp | |
| | | | | 190 | | | | | 195 | | | | | 200 | | |
| ACC | ATC | CCC | GAA | CTG | CAG | GTG | CTG | GAC | GCC | GAG | GGC | AAC | CGC | GTG | GAG | 1338 |
| Thr | Ile | Pro | Glu | Leu | Gln | Val | Leu | Asp | Ala | Glu | Gly | Asn | Arg | Val | Glu | |
| | | 205 | | | | 210 | | | | | 215 | | | | | |
| CAC | CCG | ACG | CTG | GAG | AAC | GTG | GAG | ACG | GCG | TGC | ATT | GGC | TGG | TTC | ACC | 1386 |
| His | Pro | Thr | Leu | Glu | Asn | Val | Glu | Thr | Ala | Cys | Ile | Gly | Trp | Phe | Thr | |
| | 220 | | | | | 225 | | | | | 230 | | | | | |
| CTG | GAG | TAC | CTG | CTG | CGC | CTC | TTC | TCG | TCA | CCC | AAC | AAG | CTG | CAC | TTC | 1434 |
| Leu | Glu | Tyr | Leu | Leu | Arg | Leu | Phe | Ser | Ser | Pro | Asn | Lys | Leu | His | Phe | |
| 235 | | | | | 240 | | | | | 245 | | | | | 250 | |
| GCG | CTG | TCC | TTC | ATG | AAC | ATT | GTG | GAC | GTG | CTG | GCC | ATC | CTC | CCC | TTC | 1482 |
| Ala | Leu | Ser | Phe | Met | Asn | Ile | Val | Asp | Val | Leu | Ala | Ile | Leu | Pro | Phe | |
| | | | | 255 | | | | | 260 | | | | | | 265 | |
| TAC | GTG | AGC | CTC | ACG | CTC | ACG | CAC | CTG | GGT | GCC | CGC | ATG | ATG | GAG | CTG | 1530 |
| Tyr | Val | Ser | Leu | Thr | Leu | Thr | His | Leu | Gly | Ala | Arg | Met | Met | Glu | Leu | |
| | | | 270 | | | | | 275 | | | | | 280 | | | |
| ACC | AAC | GTG | CAG | CAG | GCC | GTG | CAG | GCG | CTG | CGG | ATC | ATG | CGC | ATC | GCG | 1578 |
| Thr | Asn | Val | Gln | Gln | Ala | Val | Gln | Ala | Leu | Arg | Ile | Met | Arg | Ile | Ala | |
| | | | 285 | | | | | 290 | | | | | 295 | | | |
| CGC | ATC | TTC | AAG | CTG | GCC | CGC | CAC | TCC | TCG | GGC | CTG | CAG | ACC | CTC | ACC | 1626 |
| Arg | Ile | Phe | Lys | Leu | Ala | Arg | His | Ser | Ser | Gly | Leu | Gln | Thr | Leu | Thr | |
| | | 300 | | | | | 305 | | | | | 310 | | | | |
| TAT | GCC | CTC | AAG | CGC | AGC | TTC | AAG | GAA | CTG | GGG | CTG | CTG | CTC | ATG | TAC | 1674 |
| Tyr | Ala | Leu | Lys | Arg | Ser | Phe | Lys | Glu | Leu | Gly | Leu | Leu | Leu | Met | Tyr | |
| 315 | | | | | 320 | | | | | 325 | | | | | 330 | |
| CTG | GCA | GTG | GGT | ATC | TTC | GTC | TTC | TCT | GCC | CTG | GGC | TAC | ACC | ATG | GAG | 1722 |
| Leu | Ala | Val | Gly | Ile | Phe | Val | Phe | Ser | Ala | Leu | Gly | Tyr | Thr | Met | Glu | |
| | | | | 335 | | | | | 340 | | | | | 345 | | |
| CAG | AGC | CAT | CCA | GAG | ACC | CTG | TTT | AAG | AAC | ATC | CCC | CAG | TCC | TTC | TGG | 1770 |
| Gln | Ser | His | Pro | Glu | Thr | Leu | Phe | Lys | Asn | Ile | Pro | Gln | Ser | Phe | Trp | |
| | | | 350 | | | | | 355 | | | | | 360 | | | |
| TGG | GCC | ATC | ATC | ACC | ATG | ACC | ACC | GTC | GGC | TAC | GGC | GAC | ATC | TAC | CCC | 1818 |
| Trp | Ala | Ile | Ile | Thr | Met | Thr | Thr | Val | Gly | Tyr | Gly | Asp | Ile | Tyr | Pro | |
| | | | 365 | | | | 370 | | | | | 375 | | | | |
| AAG | ACC | ACG | CTG | AGC | AAG | CTC | AAC | GCG | GCC | ATC | AGC | TTC | TTG | TGT | GGT | 1866 |
| Lys | Thr | Thr | Leu | Ser | Lys | Leu | Asn | Ala | Ala | Ile | Ser | Phe | Leu | Cys | Gly | |
| | 380 | | | | | 385 | | | | | 390 | | | | | |
| GTC | ATT | GCC | ATC | GCC | CTG | CCC | ATC | CAC | CCC | ATC | ATC | AAC | AAC | TTT | GTC | 1914 |
| Val | Ile | Ala | Ile | Ala | Leu | Pro | Ile | His | Pro | Ile | Ile | Asn | Asn | Phe | Val | |
| 395 | | | | | 400 | | | | | 405 | | | | | 410 | |
| AGG | TAC | TAC | AAC | AAG | CAG | CGC | GTC | CTG | GAG | ACC | GCG | GCC | AAG | CAC | GAG | 1962 |
| Arg | Tyr | Tyr | Asn | Lys | Gln | Arg | Val | Leu | Glu | Thr | Ala | Ala | Lys | His | Glu | |
| | | | | 415 | | | | | 420 | | | | | 425 | | |
| CTG | GAG | CTG | ATG | GAA | CTC | AAC | TCC | AGC | AGC | GGG | GGC | GAG | GGC | AAG | ACC | 2010 |
| Leu | Glu | Leu | Met | Glu | Leu | Asn | Ser | Ser | Ser | Gly | Gly | Glu | Gly | Lys | Thr | |
| | | | 430 | | | | | 435 | | | | | 440 | | | |
| GGG | GGC | TCC | CGC | AGT | GAC | CTG | GAC | AAC | CTC | CCT | CCA | GAG | CCT | GCG | GGG | 2058 |
| Gly | Gly | Ser | Arg | Ser | Asp | Leu | Asp | Asn | Leu | Pro | Pro | Glu | Pro | Ala | Gly | |
| | | | 445 | | | | | 450 | | | | | 455 | | | |
| AAG | GAG | GCG | CCG | AGC | TGC | AGC | AGC | CGG | CTG | AAG | CTC | TCC | CAC | AGC | GAC | 2106 |
| Lys | Glu | Ala | Pro | Ser | Cys | Ser | Ser | Arg | Leu | Lys | Leu | Ser | His | Ser | Asp | |
| | 460 | | | | | 465 | | | | | 470 | | | | | |

|  |  |
|---|---|
| ACC TTC ATC CCC CTC CTG ACC GAG GAG AAG CAC CAC AGG ACC CGG CTC<br>Thr Phe Ile Pro Leu Leu Thr Glu Glu Lys His His Arg Thr Arg Leu<br>475       480     485       490 | 2154 |
| CAG AGT TGC AAG TGACAGGAGG CCCCTCAGGC AGAGATGGAC CAGGCGGTGG<br>Gln Ser Cys Lys | 2206 |
| ACAGATGGGT AGATGTGGCA GGCATGTCAT CGACAGCACA GAAGGGCTGT CCTGTGTCCC | 2266 |
| CCCAACCCTC CCCTGGACAG ACTCTGAAGG CCCTCCCGGC ACCTCTGCCA AGGCTGGGTA | 2326 |
| AGACTCCTCT ATGTTGCCTG CTGTCCAGGA GCCCGGGAGG GAGGGGTGTG CAGGAGCCGC | 2386 |
| AGGGCCGTGT GGGACGAGTG GAGGCCGCGG CCTGGCTGGC ACGAGAGCCC ACGCCCGCTT | 2446 |
| CTGTATCTCC CTCAATAAAG CCTCCTGCTC TGTGCAA | 2483 |

( 2 ) INFORMATION FOR SEQ ID NO:4:

( i ) SEQUENCE CHARACTERISTICS:
    ( A ) LENGTH: 494 AMINO ACIDS
    ( B ) TYPE: AMINO ACID
    ( C ) STRANDEDNESS:
    ( D ) TOPOLOGY: LINEAR ( i i ) MOLECULE TYPE: PROTEIN ( x i ) SEQUENCE DESCRIPTION: SEQ ID NO:4:

```
Met Asp Gly Ser Gly Glu Arg Ser Leu Pro Glu Pro Gly Ser Gln
                5                  10                  15

Ser Ser Ala Ala Ser Asp Asp Ile Glu Ile Val Val Asn Val Gly
                20                 25                  30

Gly Val Arg Gln Val Leu Tyr Gly Asp Leu Leu Ser Gln Tyr Pro
                35                 40                  45

Glu Thr Arg Leu Ala Glu Leu Ile Asn Cys Leu Ala Gly Gly Tyr
                50                 55                  60

Asp Thr Ile Phe Ser Leu Cys Asp Asp Tyr Asp Pro Gly Lys Arg
                65                 70                  75

Glu Phe Tyr Phe Asp Arg Asp Pro Asp Ala Phe Lys Cys Val Ile
                80                 85                  90

Glu Val Tyr Tyr Phe Gly Glu Val His Met Lys Lys Gly Ile Cys
                95                 100                 105

Pro Ile Cys Phe Lys Asn Glu Met Asp Phe Trp Lys Val Asp Leu
                110                115                 120

Lys Phe Leu Asp Asp Cys Cys Lys Ser His Leu Ser Glu Lys Arg
                125                130                 135

Glu Glu Leu Glu Glu Ile Ala Arg Arg Val Gln Leu Ile Leu Asp
                140                145                 150

Asp Leu Gly Val Asp Ala Ala Glu Gly Arg Trp Arg Arg Cys Gln
                155                160                 165

Lys Cys Val Trp Lys Phe Leu Glu Lys Pro Glu Ser Ser Cys Pro
                170                175                 180

Ala Arg Val Val Ala Glu Leu Ser Phe Leu Leu Ile Leu Val Ser
                185                190                 195

Ser Val Val Met Cys Met Asp Thr Ile Pro Glu Leu Gln Val Leu
                200                205                 210

Asp Ala Glu Gly Asn Arg Val Glu His Pro Thr Leu Glu Asn Val
                215                220                 225

Glu Thr Ala Cys Ile Gly Trp Phe Thr Leu Glu Tyr Leu Leu Arg
                230                235                 240

Leu Phe Ser Ser Pro Asn Lys Leu His Phe Ala Leu Ser Phe Met
                245                250                 255
```

```
Asn  Ile  Val  Asp  Val  Leu  Ala  Ile  Leu  Pro  Phe  Tyr  Val  Ser  Leu
               260                      265                          270

Thr  Leu  Thr  His  Leu  Gly  Ala  Arg  Met  Met  Glu  Leu  Thr  Asn  Val
               275                      280                          285

Gln  Gln  Ala  Val  Gln  Ala  Leu  Arg  Ile  Met  Arg  Ile  Ala  Arg  Ile
               290                      295                          300

Phe  Lys  Leu  Ala  Arg  His  Ser  Ser  Gly  Leu  Gln  Thr  Leu  Thr  Tyr
               305                      310                          315

Ala  Leu  Lys  Arg  Ser  Phe  Lys  Glu  Leu  Gly  Leu  Leu  Leu  Met  Tyr
               320                      325                          330

Leu  Ala  Val  Gly  Ile  Phe  Val  Phe  Ser  Ala  Leu  Gly  Tyr  Thr  Met
               335                      340                          345

Glu  Gln  Ser  His  Pro  Glu  Thr  Leu  Phe  Lys  Asn  Ile  Pro  Gln  Ser
               350                      355                          360

Phe  Trp  Trp  Ala  Ile  Ile  Thr  Met  Thr  Thr  Val  Gly  Tyr  Gly  Asp
               365                      370                          375

Ile  Tyr  Pro  Lys  Thr  Thr  Leu  Ser  Lys  Leu  Asn  Ala  Ala  Ile  Ser
               380                      385                          390

Phe  Leu  Cys  Gly  Val  Ile  Ala  Ile  Ala  Leu  Pro  Ile  His  Pro  Ile
               395                      400                          405

Ile  Asn  Asn  Phe  Val  Arg  Tyr  Tyr  Asn  Lys  Gln  Arg  Val  Leu  Glu
               410                      415                          420

Thr  Ala  Ala  Lys  His  Glu  Leu  Glu  Leu  Met  Glu  Leu  Asn  Ser  Ser
               425                      430                          435

Ser  Gly  Gly  Glu  Gly  Lys  Thr  Gly  Gly  Ser  Arg  Ser  Asp  Leu  Asp
               440                      445                          450

Asn  Leu  Pro  Pro  Glu  Pro  Ala  Gly  Lys  Glu  Ala  Pro  Ser  Cys  Ser
               455                      460                          465

Ser  Arg  Leu  Lys  Leu  Ser  His  Ser  Asp  Thr  Phe  Ile  Pro  Leu  Leu
               470                      475                          480

Thr  Glu  Glu  Lys  His  His  Arg  Thr  Arg  Leu  Gln  Ser  Cys  Lys
               485                      490
```

( 2 ) INFORMATION FOR SEQ ID NO:5:

( i ) SEQUENCE CHARACTERISTICS:
      ( A ) LENGTH: 30 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:5:

CGGGATCCCT CCATGACCCT CTTACCGGGA          30

( 2 ) INFORMATION FOR SEQ ID NO:6:

( i ) SEQUENCE CHARACTERISTICS:
      ( A ) LENGTH: 29 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:6:

CGGGATCCCG CTCAGTTATT GTCTCTGGT           29

( 2 ) INFORMATION FOR SEQ ID NO:7:

( i ) SEQUENCE CHARACTERISTICS:
      ( A ) LENGTH: 34 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:7:

GTCCAAGCTT GCCACCATGA CCCTCTTACC CGGA            34

( 2 ) INFORMATION FOR SEQ ID NO:8:

( i ) SEQUENCE CHARACTERISTICS:
      ( A ) LENGTH: 58 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:8:

CTAGCTCGAG TCAAGCGTAG TCTGGGACGT CGTATGGGTA GCAGTTATTG TCTCTGGT            58

( 2 ) INFORMATION FOR SEQ ID NO:9:

( i ) SEQUENCE CHARACTERISTICS:
      ( A ) LENGTH: 30 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:9:

CGGGATCCCT CCATGGACGG GTCCGGGGAG            30

( 2 ) INFORMATION FOR SEQ ID NO:10:

( i ) SEQUENCE CHARACTERISTICS:
      ( A ) LENGTH: 29 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:10:

CGGGATCCCG CTCACTTGCA ACTCTGGAG            29

( 2 ) INFORMATION FOR SEQ ID NO:11:

( i ) SEQUENCE CHARACTERISTICS:
      ( A ) LENGTH: 34 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: Oligonucleotide ( x i ) SEQUENCE DESCRIPTION: SEQ ID NO:11:

GTCCAAGCTT GCCACCATGG ACGGGTCCGG GGAG            34

( 2 ) INFORMATION FOR SEQ ID NO:12:

( i ) SEQUENCE CHARACTERISTICS:
      ( A ) LENGTH: 61 BASE PAIRS
      ( B ) TYPE: NUCLEIC ACID (C) STRANDEDNESS: SINGLE
(D) TOPOLOGY: LINEAR (ii) MOLECULE TYPE: Oligonucleotide (xi) SEQUENCE DESCRIPTION: SEQ ID NO:12:

```
CTAGCTCGAG TCAAGCGTAG TCTGGGACGT CGTATGGGTA GCACTTGCAA CTCTGGAGCC     60
G                                                                      61
```

(2) INFORMATION FOR SEQ ID NO:13:

(i) SEQUENCE CHARACTERISTICS:
(A) LENGTH: 539 AMINO ACIDS
(B) TYPE: AMINO ACID
(C) STRANDEDNESS:
(D) TOPOLOGY: LINEAR (ii) MOLECULE TYPE: PROTEIN (xi) SEQUENCE DESCRIPTION: SEQ ID NO:13:

```
Pro Ala Gly Met Thr Lys His Gly Ser Arg Ser Thr Ser Ser Leu Pro
                  5                  10                     15

Pro Glu Pro Met Glu Ile Val Arg Ser Lys Ala Cys Ser Pro Arg Val
             20                  25                 30

Arg Leu Asn Val Gly Gly Leu Ala His Glu Val Leu Trp Arg Thr Leu
         35                 40                  45

Asp Arg Leu Pro Arg Thr Arg Leu Gly Lys Leu Arg Asp Cys Asn Thr
     50                  55                  60

His Asp Ser Leu Leu Glu Val Cys Asp Asp Tyr Ser Leu Asp Asp Asn
65                      70                  75                  80

Glu Tyr Phe Phe Asp Arg His Pro Gly Ala Phe Thr Ser Ile Leu Asn
                 85                  90                      95

Phe Tyr Arg Thr Gly Arg Leu His Met Met Glu Glu Met Cys Ala Leu
             100                 105                 110

Ser Phe Ser Gln Glu Leu Asp Tyr Trp Gly Ile Asp Glu Ile Tyr Leu
         115                 120                 125

Glu Ser Cys Cys Gln Ala Arg Tyr His Gln Lys Lys Glu Gln Met Asn
     130                 135                 140

Glu Glu Leu Lys Arg Glu Ala Glu Thr Leu Arg Glu Arg Glu Gly Glu
145                 150                 155                 160

Glu Phe Asp Asn Thr Cys Cys Ala Glu Lys Arg Lys Leu Trp Asp Leu
                 165                 170                 175

Leu Glu Lys Pro Asn Ser Ser Val Ala Ala Lys Ile Leu Ala Ile Ile
             180                 185                 190

Ser Ile Met Phe Ile Val Leu Ser Thr Ile Ala Leu Ser Leu Asn Thr
         195                 200                 205

Leu Pro Glu Leu Gln Ser Leu Asp Glu Phe Gly Gln Ser Thr Asp Asn
     210                 215                 220

Pro Gln Leu Ala His Val Glu Ala Val Cys Ile Ala Trp Phe Thr Met
225                 230                 235                 240

Glu Tyr Leu Leu Arg Phe Leu Ser Ser Pro Lys Lys Trp Lys Phe Phe
                 245                 250                 255

Lys Gly Pro Leu Asn Ala Ile Asp Leu Leu Ala Ile Leu Pro Tyr Tyr
             260                 265                 270

Val Thr Ile Phe Leu Thr Glu Ser Asn Lys Ser Val Leu Gln Phe Gln
         275                 280                 285

Asn Val Arg Arg Val Val Gln Ile Phe Arg Ile Met Arg Ile Leu Arg
     290                 295                 300
```

```
Ile   Leu   Lys   Leu   Ala   Arg   His   Ser   Thr   Gly   Leu   Gln   Ser   Leu   Gly   Phe
305                           310                      315                            320

Thr   Leu   Arg   Arg   Ser   Tyr   Asn   Glu   Leu   Gly   Leu   Leu   Ile   Leu   Phe   Leu
                        325                      330                            335

Ala   Met   Gly   Ile   Met   Ile   Phe   Ser   Ser   Leu   Val   Phe   Phe   Ala   Glu   Lys
                  340                       345                            350

Asp   Glu   Asp   Asp   Thr   Lys   Phe   Lys   Ser   Ile   Pro   Ala   Ser   Phe   Trp   Trp
            355                       360                            365

Ala   Thr   Ile   Thr   Met   Thr   Thr   Val   Gly   Tyr   Gly   Asp   Ile   Tyr   Pro   Lys
            370                   375                            380

Thr   Leu   Leu   Gly   Lys   Ile   Val   Gly   Gly   Leu   Cys   Cys   Ile   Ala   Gly   Val
385                           390                      395                                  400

Leu   Val   Ile   Ala   Leu   Pro   Ile   Pro   Ile   Ile   Val   Asn   Asn   Phe   Ser   Glu
                        405                       410                            415

Phe   Tyr   Lys   Glu   Gln   Lys   Arg   Gln   Glu   Lys   Ala   Ile   Lys   Arg   Arg   Glu
                  420                       425                            430

Ala   Leu   Glu   Arg   Ala   Lys   Arg   Asn   Gly   Ser   Ile   Val   Ser   Met   Asn   Met
            435                       440                            445

Lys   Asp   Ala   Phe   Ala   Arg   Ser   Ile   Glu   Met   Met   Asp   Ile   Val   Val   Glu
      450                           455                      460

Lys   Asn   Gly   Glu   Asn   Met   Gly   Lys   Lys   Asp   Lys   Val   Gln   Asp   Asn   His
465                           470                      475                                  480

Leu   Ser   Pro   Asn   Lys   Trp   Lys   Trp   Thr   Lys   Arg   Thr   Leu   Ser   Glu   Thr
                        485                       490                            495

Ser   Ser   Ser   Lys   Ser   Phe   Glu   Thr   Lys   Glu   Gln   Gly   Ser   Pro   Glu   Lys
                  500                       505                            510

Ala   Arg   Ser   Ser   Ser   Ser   Pro   Gln   His   Leu   Asn   Val   Gln   Gln   Leu   Glu
            515                       520                            525

Asp   Met   Tyr   Asn   Lys   Met   Ala   Lys   Thr   Gln   Ser
      530                           535
```